(12) United States Patent
Kroeger et al.

(10) Patent No.: US 6,370,407 B1
(45) Date of Patent: Apr. 9, 2002

(54) SYSTEM FOR IMPROVING THE SENSITIVITY AND STABILITY OF OPTICAL POLARIMETRIC MEASUREMENTS

(75) Inventors: James K. Kroeger; Alan J. Leszinske, both of Albuquerque, NM (US)

(73) Assignee: TecMed, Incorporated, Albuquerque, NM (US)

( * ) Notice: Subject to any disclaimer, the term of this patent is extended or adjusted under 35 U.S.C. 154(b) by 0 days.

(21) Appl. No.: 09/591,955

(22) Filed: Jun. 12, 2000

Related U.S. Application Data

(60) Provisional application No. 60/145,909, filed on Jul. 27, 1999.

(51) Int. Cl.$^7$ ................................................. A61B 5/00
(52) U.S. Cl. ........................ 600/319; 600/316; 600/322
(58) Field of Search ................................ 600/318–319, 600/309–310, 331, 322, 326, 316; 356/39–42, 364

(56) References Cited

U.S. PATENT DOCUMENTS

| | | | |
|---|---|---|---|
| 3,958,560 A | 5/1976 | March | |
| 4,014,321 A | 3/1977 | March | |
| 4,721,677 A | 1/1988 | Clark, Jr. | 435/291 |
| 5,006,342 A | 4/1991 | Cleary et al. | 424/445 |
| 5,009,230 A | 4/1991 | Hutchinson | |
| 5,070,874 A | 12/1991 | Barnes et al. | |
| 5,139,023 A | 8/1992 | Stanley et al. | |
| 5,140,985 A | 8/1992 | Schroeder et al. | |
| 5,209,231 A | 5/1993 | Cote et al. | |
| 5,303,709 A | * 4/1994 | Dreher et al. | 600/476 |
| 5,313,941 A | 5/1994 | Braig et al. | |
| 5,321,265 A | 6/1994 | Block | 250/343 |
| 5,370,114 A | 12/1994 | Wong et al. | |
| 5,379,764 A | 1/1995 | Barnes et al. | |

(List continued on next page.)

OTHER PUBLICATIONS

"Noninvasive Glucose Monitoring of the Aqueous Humor of the Eye: Part 1. Measurement of Very Small Optical Rotations", by B. Rabinovitch, W. F. March, and Robert L. Adams, Diabetes Care, vol. 5, No. 3, May–Jun. 1982, pp 254–258.

(List continued on next page.)

Primary Examiner—Eric F. Winakur
Assistant Examiner—Matthew Kremer
(74) Attorney, Agent, or Firm—Cahill, Sutton & Thomas P.L.C.

(57) ABSTRACT

A polarimeter adapted for measurement of the concentration of glucose in a sample includes a laser beam passing through a first polarizer and an optical modulator and split into a measurement beam passing through a FIRST ANALYZER to a first detector coupled to a first amplifier and a reference beam passing through a SECOND ANALYZER to a second detector coupled to a second amplifier. Identical multiple filtering and summing operations are performed on outputs of the first and second amplifiers to produce a first $\Psi^2/2$ signal and a first $2\beta\Psi$ signal in response to the measurement beam and a second $\Psi^2/2$ signal and a second $2\beta\Psi$ signal in response to the reference beam. The measurement beam is stabilized by comparing the second $\Psi^2/2$ signal to a first reference signal to produce a first error signal and comparing the second $2\beta\Psi$ signal to a second reference signal to produce a second error signal. The first error signal is multiplied by a modulation signal to produce a modulation feedback signal and adding it to the second error signal to produce a combined modulation and zeroing feedback signal which drives the optical modulator so as to minimize the first and second error signals. First and second values of $\beta$ are computed from the first $\Psi^2/2$ signal and the first $2\beta\Psi$ signal without and with the sample in the path of the measurement beam, and the difference is converted to a value of glucose concentration in the sample.

31 Claims, 20 Drawing Sheets

Simplified Optics Diagram

U.S. PATENT DOCUMENTS

| | | | |
|---|---|---|---|
| 5,383,452 A | 1/1995 | Buchert | |
| 5,398,681 A | 3/1995 | Kuperschmidt | |
| 5,433,197 A | 7/1995 | Stark | |
| 5,435,309 A | 7/1995 | Thomas et al. | |
| 5,448,992 A | 9/1995 | Kuperschmidt | |
| 5,568,049 A | 10/1996 | Bucholtz | 324/244.1 |
| 6,005,916 A | * 12/1999 | Johnson et al. | 378/87 |

OTHER PUBLICATIONS

"Multispectral polarimetric glucose detection using a single Pockels cell", by Timothy W. King, Gerard L. Cote, Roger McNichols and Marcel J. Goetz, Jr., Optical Engineering, Aug. 1995, vol. 33, No. 8, pp 2746–2753.

"Microdegree Polarimetry Using A Diode Laser For Glucose Detection", by Marcel J. Goetz Jr., Martin D. Fox and Robert B. Northrop, IEEE 1992, pp. 97–98.

"A High–precision Photoelectric Polarimeter", by E. J. Gillham, Journal of Scientific Instruments, vol. 34, Nov. 1957, pp. 435–439.

"Specific Rotation of Sugar—Sugar Analysis", 3rd Edition, Browne & Zerban, John Wiley & Sons, 1941, pp. 263–293.

"Non–Invasive Optical Glucose Sensing—An Overview" by Gerard L. Coté, PhD. Journal of Clinical Engineering, vol. 22, No. 4, Jul./Aug. 1997, pp. 253–259.

"A High–Precision Photoelectric Polarimeter"by E. J. Gillham, M.A., Light Division, National Physical Laboratory, Teddington, Middlesex, Journal of Scientific Instruments, vol. 34, Nov. 1957, pp. 435–439.

"A Treatise on the Theory of Bessel Functions", by G. N. Watson, Cambridge University Press, 2nd edition, 1944.

"Bessel Functions For Engineers", by N. W. McLachlan, Oxford University Press, 1955.

Russian paper by Korolev et al., "Stabilization of the emission amplitude of semiconductor laser diodes", American Institute of Physics, 1990, pp. 863–867.

"Noninvasive Glucose Sensing Utilizing a Digital Closed–loop Polarimetric Approach", B. D. Cameron, G. L. Coté, IEEE vol. 44, No. 12, 1997, pp. 1221–1227.

"Understanding Digital Signal Processing", Richard G. Lyons, Addison–Wesley, 1997.

* cited by examiner

Light Energy Distribution

Even Frequency Waveform at 75 Deg Mod.

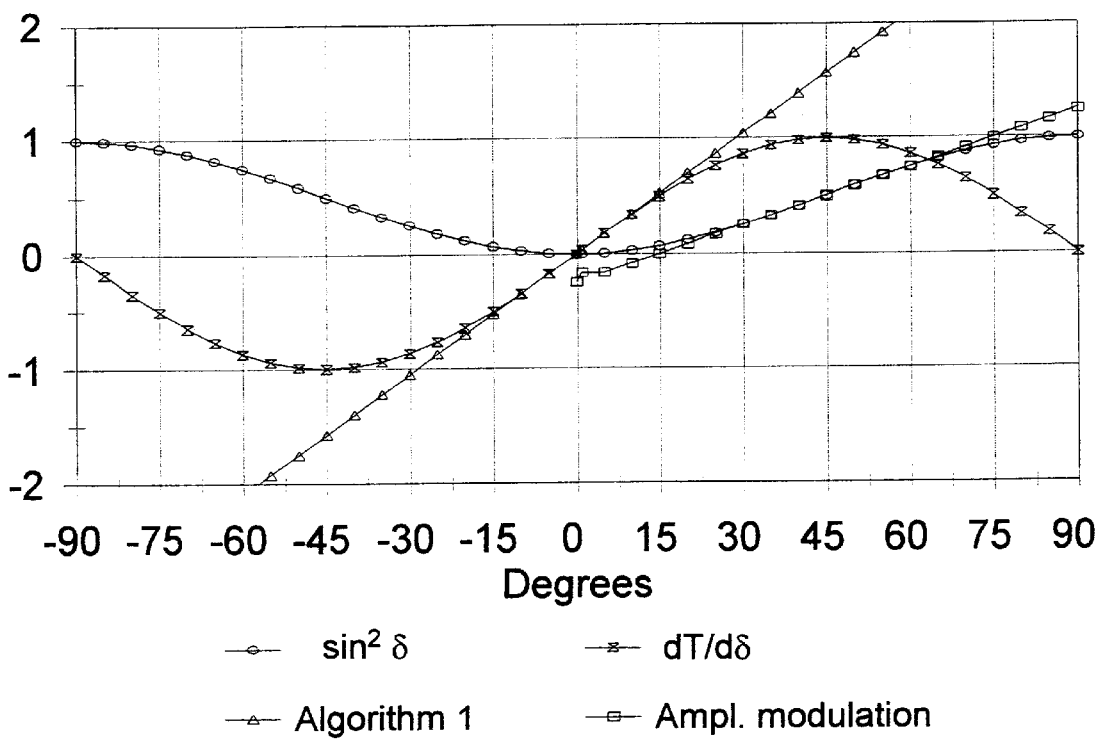

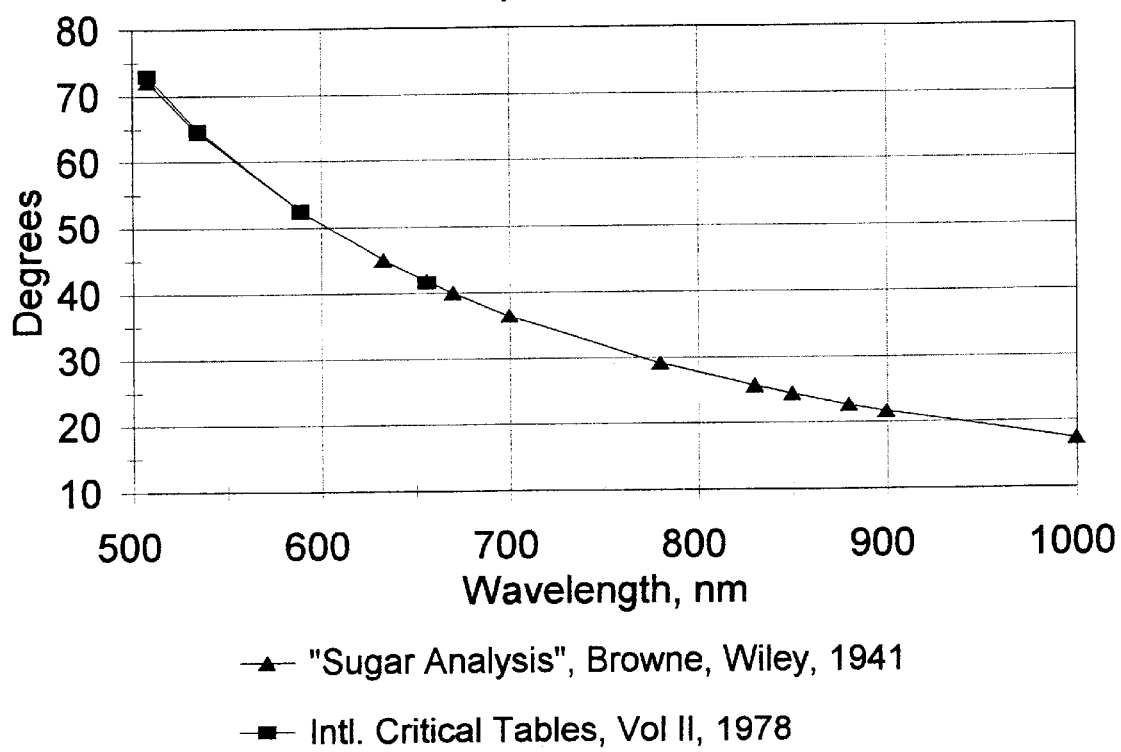

Simplified Optics Diagram

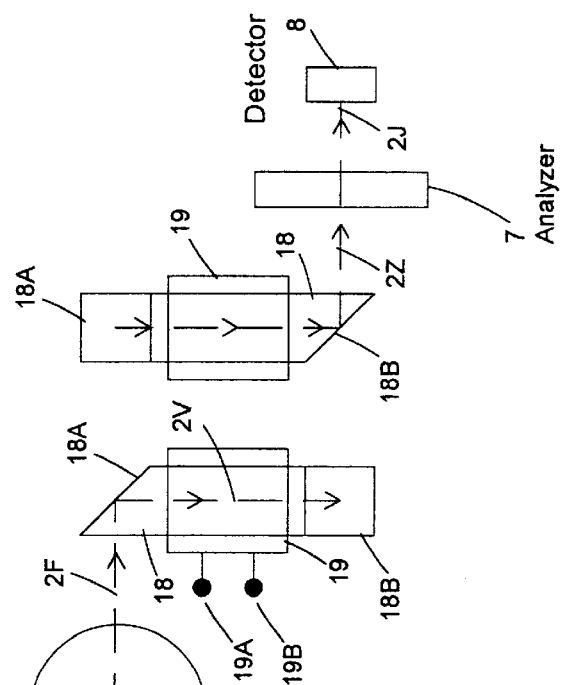
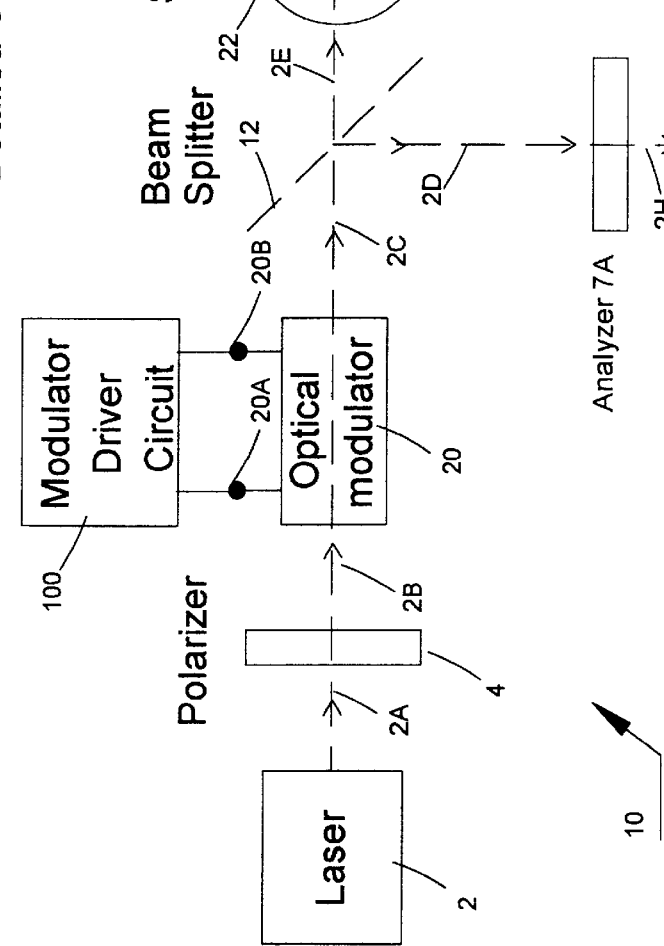
Figure 10B
Figure 10C

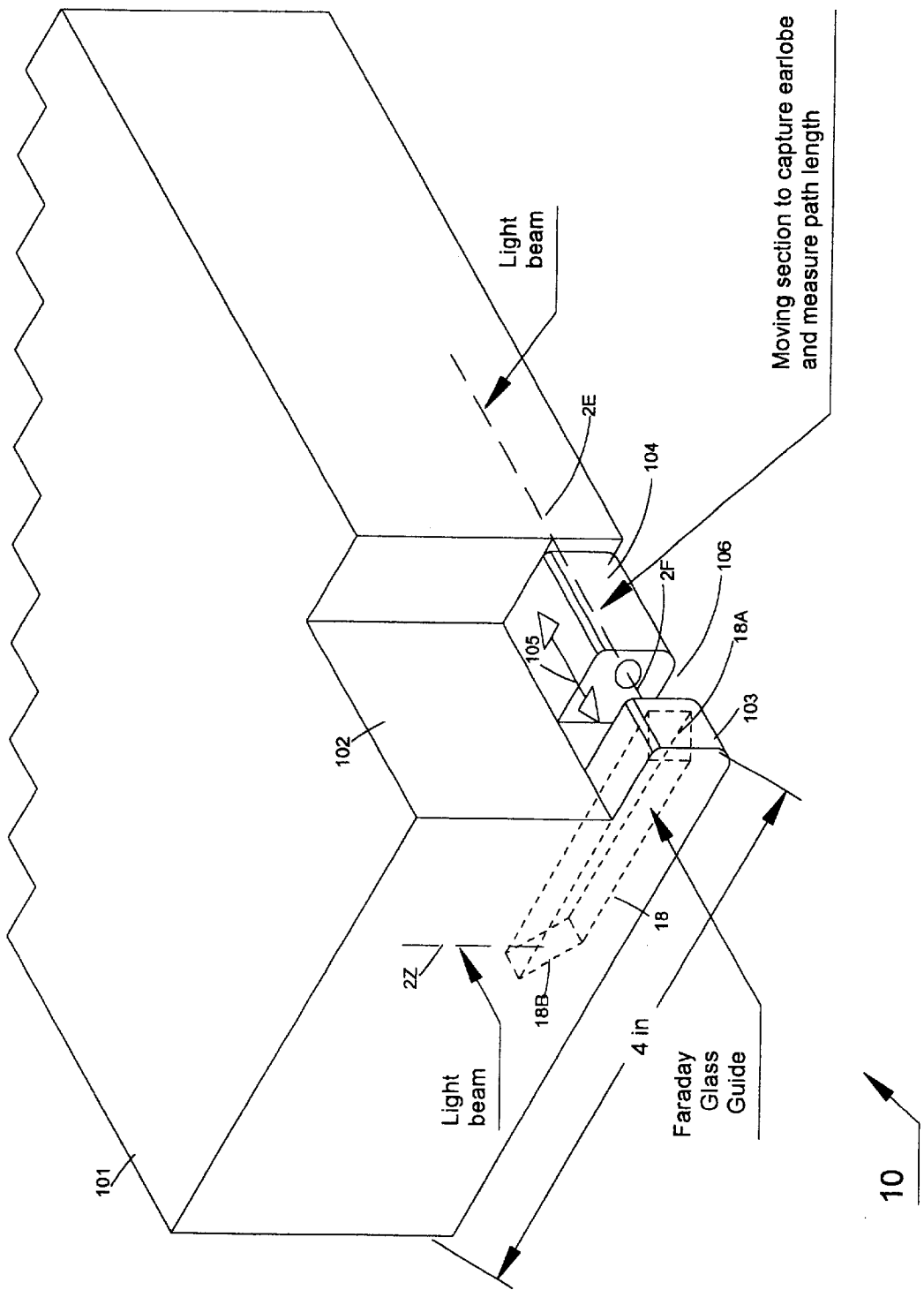

SYSTEM FOR IMPROVING THE SENSITIVITY AND STABILITY OF OPTICAL POLARIMETRIC MEASUREMENTS

CROSS REFERENCE TO RELATED APPLICATION

This application claims the benefit of prior filed co-pending U. S. Provisional Application Serial No. 60/145,909 filed Jul. 27, 1999 entitled "SYSTEM FOR FUNDAMENTALLY IMPROVING THE SENSITIVITY AND STABILITY OF OPTICAL POLARIMETRIC MEASUREMENTS, WITH SPECIFIC APPLICATION" by James K. Kroeger and Alan J. Leszinske.

BACKGROUND OF THE INVENTION

The invention relates to polarimetry, especially as applied to noninvasive measuring of blood glucose concentration in diabetics. It is known that this phenomenon offers the potential for developing a noninvasive blood glucose analyzer.

Diabetes is a disease which entails a large number of associated complications. Retinal deterioration leading to blindness and impaired circulation leading to limb amputation, kidney failure and heart disease are just some of the more serious complications. Many of these complications result from the large excursions in blood glucose concentrations common to diabetics due to dietary intake, inadequate exercise, genetic predisposition, and complicated by infrequent and inaccurate monitoring of the blood glucose levels. Current methods of in home monitoring of blood glucose involve the lancing or sticking of a finger and external measurement of the glucose content of the blood sample and or urine sampling by use of a litmus strip test comparing a color change relative to glucose concentrations.

Although many diabetes patients should use the "finger sticking" test to obtain blood for glucose concentration measurements four or more times per day, studies show that very few patients do this unless they absolutely have to, and many patients only do it a few times at the beginning of their treatment until they establish what they think is a pattern in their required medication schedule. They then stop the regular and frequent finger sticking tests and simply take their insulin injections or oral medications on the assumption that their body chemistry is thereafter constant. This leads to large changes in glucose concentration in the patient's blood, which in turn leads to a variety of serious medical consequences to the patient. For example, it is estimated that in 1996 there were over fifty thousand amputations of limbs due to complications of diabetes in the U.S.

Diabetics recover from cuts and bruises more slowly than do nondiabetics. This very real and basic discomfort also causes many diabetics to minimize the frequency of or altogether ignore blood glucose testing, resulting in a higher frequency of complications than otherwise would be the case. A small accurate device that could make blood glucose measurements on a non-invasive basis would be of great value to the diabetic in that it would greatly encourage frequent monitoring of blood glucose levels without pain.

It is well known that glucose in solution is an optically active material. That is, it will cause the plane of polarization of light traversing the solution to be rotated. The quantitative relationship between the amount of polarization rotation, the glucose concentration, and the optical path length of the solution has been clearly established. This is expressed mathematically as:

$$\{\alpha\} = \frac{100\alpha}{C*L}$$

or:

$$C = \frac{100\alpha}{\{\alpha\}*L}$$

Where:
  α is the polarization rotation in degrees;
  {α} is the specific rotation constant of glucose; ({α}=45.1 degrees per decimeter (dm) per gram per milliliter for glucose at a wavelength of 633 nanometers);
  L is the path length in the solution in dm, (where 1 dm=10 centimeters (cm);
  C is the glucose concentration in grams (g) per 100 milliliter of solution or g/dL. (From "Sugar Analysis", 3rd Edition, Browne & Zerban, John Wiley & Sons, 1941, page 263.)

For the clinically meaningful glucose concentration range from 25 to 500 mg/dL (milligrams per deciliter) and a path length of 1 cm, the observed rotation ranges from about 0.00113 degrees to 0.02255 degrees at a wavelength of 633 nanometers.

It is known that human tissue has an absorption minima in the wavelength range from about 750 nanometers to 900 nanometers. Because there are no fundamental absorption processes in this region, human tissue has a reasonable optical transmission in this region of the spectrum. Light scattering by tissue remains a problem, which may limit the path length to less than 4 mm, dependent upon the type of tissue.

All of the prior art systems using crossed polarizers use only a single frequency, usually in conjunction with a null control system and a lock in amplifier that operates only at that single frequency. The prior art null compensation techniques all involve inserting a sample between the first and second polarizers and driving a Faraday modulator to reestablish the extinction condition. The problem with the prior techniques of establishing a null condition at extinction in a system using crossed polarizers is that the laser, optical modulator, and other components have parameters which drift from the time that the null condition or extinction is initially established and the time at which the sample to be measured is placed between the polarizers and an extinction condition is reestablished to determine the phase rotation caused by the sample.

According to the article "Non-Invasive Optical Glucose Sensing—An Overview" by Gerard L. Coté, PhD. Journal of Clinical Engineering, Vol. 22, No. 4, July/August 1997, a path length of 4 mm through human soft tissue (other than the eye) attenuates or scatters 95% of the signal. We conducted tests to confirm the general claims by Coté and found that both scattering and absorption are strongly wavelength dependent.

Because of the impracticality of using prior art devices and techniques to accurately measure such a small signal, the prior art use of polarimetry to measure glucose concentration levels in human tissue has been based primarily on passing light through the transparent tissue of the anterior chamber of the human eye.

The prior art fails to provide any practical, workable polarimeter system which can consistently provide accurate measurements of the glucose level in human tissue because of the inadequate sensitivity and the large degree of instability of the prior art devices. There is a strong but unmet need for a practical, reliable system which overcomes the problems of the prior art to provide a practical, reasonably priced, noninvasive system for measurement of human glucose levels.

SUMMARY OF THE INVENTION

Accordingly, it is an object of the invention to provide a device capable of consistently and accurately measuring the concentration of an optically active ingredient in a sample.

It is another object of the invention to provide a practical, economical device for noninvasive measurement of glucose levels in diabetics.

It is another object of the invention to avoid instrument instability problems which have in part prevented success of prior attempts to provide a practical system using polarimetry to noninvasively measure blood glucose levels in diabetics.

It is another object of the invention to provide a device capable of measuring an optically sensitive ingredient in biological tissue in a noninvasive manner more accurately than has been achieved in the prior art.

It is another object of this invention to provide a new very sensitive and very stable polarization spectrometer which has applications in certain types of chemical analysis.

It is another object of the invention to provide a device capable of measuring optical rotation in the presence of large percentages of more than about 95% scattered light.

It is another object of the invention to provide an improved polarimeter which is more sensitive and more stable than prior art polarimeters.

Briefly described, and in accordance with one embodiment thereof, the invention provides a system for polarimetric measurement of the concentration of a substance, such as glucose, in a sample, including a laser beam passing through a first polarizer and an optical modulator and then split into (1) a measurement beam which is analyzed and directed to a first detector coupled to a first amplifier, and (2) a reference beam which is analyzed and directed to a second detector coupled to a second amplifier. Identical multiple filtering and summing operations are performed on outputs of the first and second amplifiers to produce a first $\Psi^2/2$ signal and a first $2\beta\Psi$ signal in response to the measurement beam and a second $\Psi^2/2$ signal and a second $2\beta\Psi$ signal in response to the reference beam. The measurement beam is stabilized by a first control loop that compares the second $\Psi^2/2$ signal to a first reference signal to produce a first error signal and a second control loop that compares the second $2\beta\Psi$ signal to a second reference signal to produce a second error signal. The first error signal is multiplied by a modulation signal to produce a modulation feedback signal and adding it to the second error signal to produce a combined modulation and zeroing feedback signal. The optical modulator then is driven in response to the combined modulation and zeroing feedback signal to minimize the first and second error signals. A first value of $\beta$ is computed from the first $\Psi^2/2$ signal and the first $2\beta\Psi$ signal with no sample in the path of the measurement beam, and a second value of $\beta$ is computed from the first $\Psi^2/2$ signal and the first $2\beta\Psi$ signal with the sample in the path of the measurement beam. The difference between the first and second values of $\beta$ is converted to a value of concentration of the optically active substance in the sample by reference to a look-up table or algorithm. Both a primarily hardware implementation of the invention and a primarily sofware/firmware DSP implementation of the invention are disclosed.

BRIEF DESCRIPTION OF THE DRAWINGS

FIG. 8 is a graph useful in comparing the sensitivity of the stabilization loop of the present invention to that of the prior art.

FIG. 9 is a graph of the known relationship of specific rotation of glucose to wavelength.

FIG. 10B is a detailed optics diagram of one preferred embodiment of the polarimeter system of FIG. 11A.

FIG. 10C is a side view diagram of a portion of the system of FIG. 10B.

FIG. 15 is a perspective drawing of an implementation of FIG. 10B adapted to receive an ear lobe as the sample.

DETAILED DESCRIPTION OF THE PREFERRED EMBODIMENTS

Figure 1:
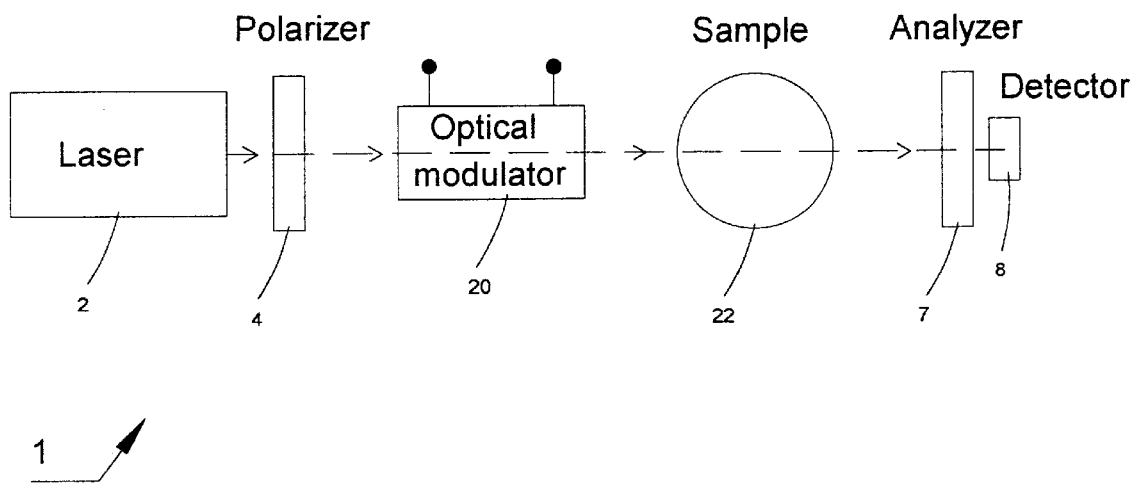
FIG. 1 is an optical schematic of a basic prior art polarimeter system.

The components of a typical prior art polarimeter, shown in FIG. 1, include a laser 2 which is a monochromatic light source, the output of which is transmitted to a polarizer 4. The light passing from polarizer 4 is called polarized light. The polarized beam passes through an optical modulator 20 which can be used to rotate the polarized light in a totally electronic manner, as opposed to the conventional method of mechanically rotating polarizer 4 or an analyzer 7 to effect the measurement. The laser beam then passes through an analyzer 7. The second polarizer of a pair of crossed polarizers is called an "analyzer". Analyzer 7 is said to "analyze" the polarized light from the optical modulator 20. The light emanating from analyzer 7 impinges on a suitable detector 8, such as a silicon PIN photodiode, which produces an output signal 11 that represents the amount of light that is transmitted through the entire polarimeter.

As the wavelength of light is increased, the specific rotation $\{\alpha\}$ decreases, to a value of 21.7 at a wavelength of 900 nanometers (see FIG. 9). At 900 nm and a path length of 4 mm, the observed rotation is 0.00022° at a concentration of 25 mg/dL. We have discovered that a useable system must have a basic sensitivity of the order of about 0.00001 degrees, or 10 micro degrees. To be useful, the system must also be stable to 0.00001 degrees. Using the stabilization methods described herein, we can achieve this required stability.

Prior art polarimeter 1 is capable of analyzing polarized light. Its precision is limited by the quality of polarizer 4 and analyzer 7 and the stability of all of the components, especially laser diode 2, and the capability of determining the "position" of the intensity minimum at the detector.

Mathematical Algorithms for Improved Polarimetry

The following mathematical analysis will show the development of new algorithms which can be used to fundamentally improve both the sensitivity and stability of optical polarimetric measurements.

The transmission of light through two polarizers is given by:

$$I/I_0 = K_0 \cos^2 \theta + K_{90} \sin^2 \theta \qquad \text{Eq.(1)}$$

where

I is the light transmitted through the polarizers $I_0$ is the light incident upon the polarizers $\theta$ is the relative angle between the two polarizers, $K_0$ is the maximum transmission at $\theta=0°$, and $K_{90}$ is the minimum transmission, or extinction, at $\theta=90°$.

Applying the trigonometric identity $$\sin^2 \theta + \cos^2 \theta = 1,$$

$$\cos^2 \theta = 1 - \sin^2 \theta,$$

then $$I/I_0 = K_0 - K_0 \sin^2 \theta + K_{90} \sin^2 \theta.$$

and, $$I/I_0 = K_0 - (K_0 - K_{90}) \sin^2 \theta. \qquad \text{Eq.(2)}$$

Using another identity:

$$\cos(2\theta) = 1 - 2 \sin^2 \theta$$

or $$\sin^2 \theta = 1/2 - 1/2 \cos(2\theta) \qquad \text{Eq.(3)}$$

then $$I/I_0 = (K_0 + K_{90})/2 + (K_0 - K_{90})/2 \cos(2\theta). \qquad \text{Eq.(4)}$$

Because we are operating at the 90° extinction point of the crossed polarizers, let $$\theta = (\delta + \pi/2) \text{ or } 2\theta = (2\delta + \pi), \text{ so}$$

$$I/I_0 = (K_0 + K_{90})/2 + (K_0 - K_{90})/2 \cos(2\delta + \pi). \qquad \text{Eq.(5)}$$

Using the identity $$\cos(2\delta + \pi) = \cos 2\delta \cos \pi - \sin 2\delta \sin \pi$$

$$\cos(2\theta) = \cos(2\delta + \pi) = -\cos(2\delta),$$

then $$I/I_0 = (K_0 + K_{90})/2 - (K_0 - K_{90})/2 \cos(2\delta), \qquad \text{Eq.(6)}$$

where $\delta$ is the modulation angle measured from the 90° extinction point of the crossed polarizers.

Note that applying the identity in Eq.(3), to Eq.(6) yields the mathematically identical expression $$I/I_0 = K_{90} + (K_0 - K_{90}) \sin^2 \delta. \qquad \text{Eq.(7)}$$

The series expansion of $\cos(2\delta)$ is $$\cos 2\delta = (1 - 2\delta^2 + 2/3 \, \delta^4 - 4/45 \, \delta^6 + 2/315 \, \delta^8 + \ldots). \qquad \text{Eq.(8)}$$

Now if we let $$\delta = \beta + \Psi_m \cos(\omega t), \qquad \text{Eq.(9)}$$

where $\beta$ represents the polarization rotation angle that we wish to measure (from extinction), and $\Psi_m \cos(\omega t)$ represents sinusoidal modulation of the polarized light due to an optical modulator. $\omega$ represents the modulation frequency in radians. $\Psi_m$ is a constant equal to the maximum angle of a given modulation from extinction. (The standard literature uses $\alpha$ to represent the measured polarization rotation angle and $\{\alpha\}$ to represent the specific rotation of a substance. $\beta$ is used herein for the measured polarization rotation angle in order to avoid confusion.)

The binomial expansion of Eq.(9) is $$\delta^2 = \beta^2 + 2\beta\Psi_m \cos(\omega t) + \Psi_m^2 \cos^2(\omega t)$$

$$\delta^4 = \beta^4 + 4\beta\Psi_m^3 \cos(\omega t) + 6\beta^2\Psi_m^2 \cos^2(\omega t) + 4\beta\Psi_m^3 \cos^3(\omega t) + \Psi_m^4 \cos^4(\omega t)$$

$$\delta^6 = \beta^6 + 6\beta^5\Psi_m \cos(\omega t) + 15\beta^4\Psi_m^2 \cos^2(\omega t) + 20\beta^3\Psi_m^3 \cos^3(\omega t) + 15\beta^2\Psi_m^4 \cos^4(\omega t) + 6\beta\Psi_m^5 \cos^5(\omega t) + \Psi_m^6 \cos^6(\omega t)$$

$$\delta^8 = \beta^8 + 8\beta^7\Psi_m \cos(\omega t) + 28\beta^6\Psi_m^2 \cos^2(\omega t) +$$

$$56\beta^5\Psi_m^3 \cos^3(\omega t) + 70\beta^4\Psi_m^4 \cos^4(\omega t) +$$

$$56\beta^3\Psi_m^5 \cos^5(\omega t) + 28\beta^2\Psi_m^6 \cos^6(\omega t)$$

$$+ 8\beta\Psi_m^7 \cos^7(\omega t) + \Psi_m^8 \cos^8(\omega t)$$

Substituting this binomial expansion into Eq.(8) we have $$\cos 2\delta = \{1 - 2\beta^2 + 2/3\beta^4 - 4/45\beta^6 + 2/315\beta^8\} - \{4\beta\Psi_m + 8/3\beta^3\Psi_m - 8/15\beta^5\Psi_m + 16/315\beta^7\Psi_m\}\cos(\omega t)$$

$$-\{2\Psi_m^2 - 4\beta^2\Psi_m^2 + 4/3\beta^4\Psi_m^2 - 8/45\beta^6\Psi_m^2\}\cos^2(\omega t) + \{8/3\beta\Psi_m^3 - 16/9\beta^3\Psi_m^3 + 16/45\beta^5\Psi_m^3\}\cos^3(\omega t)$$

$$+\{2/3\Psi_m^4 - 4/3\beta^2\Psi_m^4 + 4/9\beta^4\Psi_m^4\}\cos^4(\omega t) - \{8/15\beta\Psi_m^5 + 16/45\beta^3\Psi_m^5\}\cos^5(\omega t)$$

$$-\{4/45\Psi_m^6 + 8/45\beta^2\Psi_m^6\}\cos^6(\omega t) + \{16/315\beta\Psi_m^7\}\cos^7(\omega t)$$

$$+\{2/315\Psi_m^8\}\cos^8(\omega t) - \ldots \qquad \text{Eq.(10)}$$

Recognizing the following series:

$$\sin 2\beta = (2\beta - 4/3\beta^3 + 4/15\beta^5 - 8/315\beta^7 + \ldots) \qquad \text{Eq.(11)}$$

$$\cos 2\beta = (1 - 2\beta^2 + 2/3\beta^4 - 4/45\beta^6 + 2/315\beta^8 + \ldots) \qquad \text{Eq.(12)}$$

We can factor Eq.(10) to produce $$\cos 2\delta = \cos 2\beta - 2\Psi_m \{\sin 2\beta\}\cos(\omega t) - 2\Psi_m^2 \{\cos 2\beta\}\cos^2(\omega t) + 4/3\Psi_m^3 \{\sin 2\beta\}\cos^3(\omega t)$$

$$+2/3\Psi_m^4 \{\cos 2\beta\}\cos^4(\omega t) - 4/15\Psi_m^5 \{\sin 2\beta\}\cos^5(\omega t) - 4/45\Psi_m^6 \{\cos 2\beta\}\cos^6(\omega t)$$

$$+8/315\Psi_m^7 \{\sin 2\beta\}\cos^7(\omega t) + 2/315\Psi_m^8 \{\cos 2\beta\}\cos^8(\omega t) - \text{Eq.(13)}$$

For the higher power cosine terms of Eq.(13) with only one or two terms containing $\beta$, it is not evident that $\beta$ follows a series. We have calculated the binomial expansion of Eq.(8) for 7 terms of the cos $2\delta$ series which provides Eq.(13) out to the $\cos^{14}(\omega t)$ term. The $\beta$ terms in $\cos^6(\omega t)$ through $\cos^8(\omega t)$ are actually alternating series of cos $2\beta$ and sin $2\beta$. Applying the following expressions of cosine powers as cosines of multiple angles, $\cos^2 x = 1/2(1 + \cos 2x)$ $\cos^3 x\, 1/4(3 \cos x + \cos 3x)$ $\cos^4 x\, 1/8(3 + 4 \cos 2x + \cos 4x)$ $\cos^5 x\, 1/16(10 \cos x + 5 \cos 3x + \cos 5x)$

. . .

For odd powers:

$$\cos^{2n-1} x = 1/(2^{2n-2}) \sum_{k=0}^{n-1} \frac{(2n-1)!}{k!(2n-1-k)!} \cos(2n-2k-1)x \quad (n=1,2,\ldots)$$

For even powers:

$$\cos^{2n} x = 1/(2^{2n}) \left\{ \sum_{k=0}^{n-1} \frac{2n!}{k!(2n-k)!} \cos(2n-2k)x + \frac{2n!}{n!(2n-k)!} \right\} \quad (n=1,2,\ldots)$$

to Eq.(13) yields cos $2\delta = (1 - \Psi_m^2 + 1/4\Psi_m^4 - 1/36\Psi_m^6 + 1/576\Psi_m^8 - \ldots)$cos $2\beta - (2\Psi_m - \Psi_m^3 + 1/6\Psi_m^5 - 1/72\Psi_m^7 + \ldots)$ sin $2\beta$ cos($\omega t$)

$-(\Psi_m^2 - 1/3\Psi_m^4 + 1/24\Psi_m^6 - 1/360\Psi_m^8 + \ldots)$cos $2\beta$ cos($2\omega t$) $+(1/3\Psi_m^3 - 1/12\Psi_m^5 + 1/120\Psi_m^7 - \ldots)$sin $2\beta$ cos($3\omega t$)

$+(1/12\Psi_m^4 - 1/60\Psi_m^6 + 1/720\Psi_m^8 - \ldots)$cos $2\beta$ cos($4\omega t$) $-(1/60\Psi_m^5 - 1/360\Psi_m^7 + \ldots)$sin $2\beta$ cos($5\omega t$)

$-(1/360\Psi_m^6 - 1/2520\Psi_m^8 + \ldots)$cos $2\beta$ cos($6\omega t$) $+(1/2520\Psi_m^7 - \ldots)$sin $2\beta$ cos($7\omega t$)

$+(1/20160\Psi_m^8 - \ldots)$cos $2\beta$ cos($8\omega t$) $- \ldots$     Eq.(14)

The general form of the Bessel Function series expansion is, $$J_n(x) = x^n \sum_{k=0}^{\infty} \frac{(-1)^k x^{2k}}{2^{2k+n} k!(n+k)!} \quad \text{Eq.(15)}$$

and for $J_n(2x)$, we have $$J_n(2x) = \sum_{k=0}^{\infty} \frac{(-1)^k x^{2k+n}}{k!(n+k)!} \quad \text{Eq.(16)}$$

Expanding Eq.(16) for n=0 to 8 yields, $J_0(2x) = 1 - x^2 + 1/4 x^4 - 1/36 x^6 + 1/576 x^8 - \ldots$     Eq.(17)

$J_1(2x) = x - 1/2 x^3 + 1/12 x^5 - 1/144 x^7 + \ldots$     Eq.(18)

$J_2(2x) = 1/2 x^2 - 1/6 x^4 + 1/48 x^6 - 1/720 x^8 + \ldots$     Eq.(19)

$J_3(2x) = 1/6 x^3 - 1/24 x^5 + 1/240 x^7 - \ldots$     Eq.(20)

$J_4(2x) = 1/24 x^4 - 1/120 x^6 + 1/1440 x^8 - \ldots$     Eq.(21)

$J_5(2x) = 1/120 x^5 - 1/720 x^7 + \ldots$     Eq.(22)

$J_6(2x) = 1/720 x^6 - 1/5040 x^8 + \ldots$     Eq.(23)

$J_7(2x) = 1/5040 x^7 - \ldots$     Eq.(24)

$J_8(2x) = 1/40320 x^8 - \ldots$     Eq.(25)

Inspecting Eq.(14), we see that the first series term is equal to $J_0(2x)$ and the following series terms are equal to $2 J_n(2x)$. repeating Eq.(6)

$I/I_0 = (K_0 + K_{90})/2 - (K_0 - K_{90})/2 \cos(2\delta)$     Eq.(6)

inserting the Bessel Eq.(17–25) into Eq.(14), and the resulting cos($2\delta$) expansion into Eq.(6), we have $I/I_0 = (K_0 + K_{90})/2 - (K_0 - K_{90})/2 \{J_0(2\Psi_m)\cos 2\beta - 2J_1(2\Psi_m)\sin 2\beta \cos(\omega t) - 2J_2(2\Psi_m)\cos 2\beta \cos(2\omega t) + 2J_3(2\Psi_m)\sin 2\beta \cos(3\omega t)$ $+ 2J_4(2\Psi_m)\cos 2\beta \cos(4\omega t) - 2J_5(2\Psi_m)\sin 2\beta \cos(5\omega t) - 2J_6(2\Psi_m)\cos 2\beta \cos(6\omega t) + 2J_7(2\Psi_m)\sin 2\beta \cos(7\omega t)$ $+ 2J_8(2\Psi_m)\cos 2\beta \cos(8\omega t) - \ldots\}$.     Eq.(26)

Multiplying through by $I_0$ and $(K_0 - K_{90})/2$, we now have the polarimeter output light intensity I expressed in terms of $K_0$, $K_{90}$, $I_0$, $\Psi$, and $\beta$ for each individual output frequency (Eq. 27). For $\beta = 0$ and $\Psi = 0$, all of the frequency terms are zero and the DC term reduces to $K_{90}$, the extinction of the polarizers, as expected.

$I = I_0(K_0 + K_{90})/2 - I_0(K_0 - K_{90})/2 \{J_0(2\Psi_m)\cos 2\beta\} + I_0(K_0 - K_{90})\{J_1(2\Psi_m)\sin 2\beta\}\cos(\omega t)$ $+ I_0(K_0 - K_{90})\{J_2(2\Psi_m)\cos 2\beta\}\cos(2\omega t) - I_0(K_0 - K_{90})\{J_3(2\Psi_m)\sin 2\beta\}\cos(3\omega t)$ $- I_0(K_0 - K_{90})\{J_4(2\Psi_m)\cos 2\beta\}\cos(4\omega t) + I_0(K - K_{90})\{J_5(2\Psi_m)\sin 2\beta\}\cos(5\omega t)$ $+ I_0(K_0 - K_{90})\{J_6(2\Psi_m)\cos 2\beta\}\cos(6\omega t) - I_0(K_0 - K_{90})\{J_7(2\Psi_m)\sin 2\beta\}\cos(7\omega t)$ $- I_0(K_0 - K_{90})\{J_8(2\Psi_m)\cos 2\beta\}\cos(8\omega t) + \ldots$     Eq.(27)

The maximum clinical glucose concentration of 500 mg/dL, measured at a wavelength of 633 nm and a path length of 10 mm, yields a rotation angle of $\beta = 0.0225$ degrees. (Actual human in vivo measurements will generally have longer wavelengths and shorter path lengths, each of which will reduce the maximum rotation angle at 500 mg/dL.) At the worst case angle of 0.0225 degrees, the errors in replacing the sin and cos functions are:

sin $2\beta$ with $2\beta$, error $< 1 \times 10^{-10}$ cos $2\beta$ with 1, error $< 0.5 \times 10^{-7}$ With these approximations Eq.(27) becomes $I = I_0(K + K_{90})/2 - I_0(K_0 - K_{90})/2\{J_0(2\Psi_m)\} + I_0(K_0 - K_{90})\{J_1(2\Psi_m)2\beta\}\cos(\omega t) + I_0(K_0 - K_{90})\{J_2(2\Psi_m)\}\cos(2\omega t)$ $- I_0(K_0 - K_{90})\{J_3(2\Psi_m)2\beta\}\cos(3\omega t) - I_0(K_0 - K_{90})\{J_4(2\Psi_m)\}\cos(4\omega t)$ $+ I_0(K_0 - K_{90})\{J_5(2\Psi_m)2\beta\}\cos(5\omega t) + I_0(K_0 - K_{90})\{J_6(2\Psi_m)\}\cos(6\omega t) - I_0(K_0 - K_{90})\{J_7(2\Psi_m)2\beta\}\cos(7\omega t)$ $- I_0(K_0 - K_{90})\{J_8(2\Psi_m)\}\cos(8\omega t) + \ldots$     Eq.(28)

Sensitivity

An early paper by E. J. Gillham, "A High-Precision Photoelectric Polarimeter" M. A., Light Division, National Physical Laboratory, Teddington, Middlesex, Journal of Scientific Instruments, Vol. 34, November 1957, investigated the sensitivity of a polarimeter.

Multiplying Eq.(6) by $I_0$ and taking the derivatives, $$I=I_0(K_0+K_{90})/2-(K_0-K_{90})/2 \cos(2\delta) \qquad \text{Eq.(29)}$$

$$dI/d\delta=I_0(K_0-K_{90})\sin(2\delta), \text{ and} \qquad \text{Eq.(30)}$$

$$d^2I/d\delta^2=2 I_0(K_0-K_{90})\cos(2\delta). \qquad \text{Eq.(31)}$$

Solving Eq.(31) for $d^2I/d\delta^2=0$ indicates that the maximum sensitivity of $dI/d\delta$ is at $\pm 45°$ modulation from extinction as Gillham stated. Although the maximum sensitivity occurs at a modulation of $\pm 45°$, Gillham stated that precision is maximized at small modulation angles. Factors affecting precision are noise fluctuations, e.g. light intensity fluctuations and mechanical vibrations. Gillham spent several paragraphs discussing these tradeoffs and finally recommended 3° as a modulation angle.

A new sensitivity algorithm will be developed from the following mathematical analysis. Referring to the odd Bessel expansions from Eq.(17–25), $$J_1(2x)=x-1/2x^3+1/12x^5-1/144x^7+\ldots \qquad \text{Eq.(18)}$$

$$J_3(2x)=1/6x^3-1/24x^5+1/240x^7-\ldots \qquad \text{Eq.(20)}$$

$$J_5(2x)=1/120x^5-1/720x^7+\ldots \qquad \text{Eq.(22)}$$

$$J_7(2x)=1/5040x^7-\ldots \qquad \text{Eq.(24)}$$

If we multiply each odd Bessel function by its order and then sum, the result is equal to one half of the Bessel abscissa, $$\tfrac{1}{2}(2x)=x=1*J_1(2x)+3*J_3(2x)+5*J_5(2x)+7*J_7(2x)+\ldots \qquad \text{Eq.(32)}$$

Eq.(32) can be shown if we inspect the Bessel series:

| | | | | | |
|---|---|---|---|---|---|
| $1*J_1(2x)$ = | $x$ | $-1/2x^3$ | $+2/24x^5$ | $-5/720x^7$ | $+\ldots$ |
| $3*J_3(2x)$ = | | $+1/2x^3$ | $-3/24x^5$ | $+9/720x^7$ | $-\ldots$ |
| $5*J_5(2x)$ = | | | $+1/24x^5$ | $-5/720x^7$ | $+\ldots$ |
| $7*J_7(2x)$ = | | | | $+1/720x^7$ | $-\ldots$ |
| Sum = | $x$ | $+0$ | $+0$ | $+0$ | $+\ldots$ |

For the even Bessel expansions from Eq.(17–25), excluding the $J_0$ series, $$J_2(2x)=1/2x^2-1/6x^4+1/48x^6-1/720x^8+\ldots \qquad \text{Eq.(19)}$$

$$J_4(2x)=1/24x^4-1/120x^6+1/1440x^8-\ldots \qquad \text{Eq.(21)}$$

$$J_6(2x)=1/720x^6-1/5040x^8+\ldots \qquad \text{Eq.(23)}$$

$$J_8(2x)=1/40320x^8-\ldots \qquad \text{Eq.(25)}$$

If we multiply each even Bessel function by the square of one half of its order and then sum, the result is one eighth of the Bessel abscissa squared, $$1/8(4x^2)=1/2x^2=1^2*J_2(2x)+2^2*J_4(2x)+3^2*J_6(2x)+4^2*J_8(2x)+\ldots \qquad \text{Eq.(33)}$$

Aiain this can be shown if we inspect the Bessel series:

| | | | | | |
|---|---|---|---|---|---|
| $1^2*J_2(2x)$ = | $1/2x^2$ | $-1/6x^4$ | $+15/720x^6$ | $-7/5040x^8$ | $+\ldots$ |
| $2^2*J_4(2x)$ = | | $+1/6x^4$ | $-24/720x^6$ | $+14/5040x^8$ | $-\ldots$ |
| $3^2*J_6(2x)$ = | | | $+9/720x^6$ | $-9/5040x^8$ | $+\ldots$ |
| $4^2*J_8(2x)$ = | | | | $+2/5040x^8$ | $-\ldots$ |
| Sum = | $1/2x^2$ | $+0$ | $+0$ | $+0$ | $+\ldots$ |

For more information on Bessel formulas, see "A Treatise on the Theory of Bessel Functions", by G. N. Watson, Cambridge University Press, 2nd edition, 1944 and "Bessel Functions For Engineers", by N. W. McLachlan, Oxford University Press, 1955.

By using multiple bandpass filters in the time domain, or a Fast Fourier Transform (FFT) into the frequency domain, or other mathematical signal processing methodologies, we can obtain output signals that represent the magnitudes of each of the frequency coefficients in Eq.(28). For an AC coupled system, the DC term is eliminated. If we use the odd frequency terms of Eq.(28) and apply the Bessel formula Eq.(32), we obtain the following new algorithm:

Algorithm 1:

$$A_1=2\beta\Psi_m=1*Z_1 \cos(\omega t)-3*Z_3 \cos(3\omega t)+5*Z_5 \cos(5\omega t)-7*Z_7 \cos(7\omega t)+\ldots \qquad \text{Eq.(34)}$$

where $Z_1$, $Z_3$, $Z_5$, $Z_7$, ... represent the magnitudes of the specified odd frequencies.

$A_1$ is a computed signal from application of this algorithm to the individual odd frequency output signals. The alternating signs arise from the frequency terms, not from Bessel formula Eq.(32).

If we use the even frequency terms of Eq.(28) and apply the Bessel formnula Eq.(33), we obtain another new algorithm:

Algorithm 2:

$$A_2=(1/2)\omega_m^2\approx 1*Y_2 \cos(2\omega t)-2^2*Y_4 \cos(4\omega t)+3^2*Y_6 \cos(6\omega t)-4^2*Y_8 \cos(8\omega t)+\ldots \qquad \text{Eq.(35)}$$

where $Y_2$, $Y_4$, $Y_6$, $Y_8$, ... represent the magnitudes of the specified even frequencies.

$A_2$ is a computed signal from application of this algorithm to the individual even frequency output signals. The alternating signs arise from the frequency terms, not from Bessel formula Eq.(33).

Physical understanding of the Algorithms

From the trigonometric identity $$\sin^2\delta=\tfrac{1}{2}-\tfrac{1}{2}\cos 2\delta \qquad \text{Eq.(36)}$$

and using only the first term of the cos $2\delta$ expansion from Eq.(7), $$\cos 2\delta \approx 1-2\delta^2 \qquad \text{Eq.(37)}$$

then $$\sin^2\delta \approx \delta^2 \qquad \text{Eq.(38)}$$

repeating Eq.(9)

$$\delta=\beta+\Psi_m \cos(\omega t) \qquad \text{Eq.(9)}$$

we have $$\sin^2\delta \approx \delta^2=\beta 2\beta\Psi_m \cos(\omega t)+\Psi_m^2 \cos^2(\omega t). \qquad \text{Eq.(39)}$$

Applying the identity $\cos 2x=2 \cos^2 x-1$ to Eq.(39), $$\sin^2\delta \approx \delta^2=\beta^2+2\beta\Psi_m \cos(\omega t)+\Psi_m^2/2+\Psi_m^2/2 \cos(2\omega t). \qquad \text{Eq.(40)}$$

If we look at the modulated light output of two optically crossed polarizers at a PIN photodiode current-to-voltage operational amplifier output, we can see the physical significance of the four terms of Eq.(40) on an oscilloscope:

$\beta^2$: As the analyzer is moved away from extinction, we can see the DC component of the extinction voltage rise due to this term.

$2\beta\omega_m \cos(\omega t)$: A sinusoidal term, at the modulating frequency, that represents the product of our desired measurement, $\beta$, and the sinusoidal amplitude, $\Psi_m$. $2\Psi_m \cos(\omega t)$ is the carrier for $\beta$. Not easy to see except for large $\beta$ because it is mixed with a double frequency term. It becomes clear if the output of a bandpass filter centered at frequency wt is observed as $\beta$ is varied.

$\Psi_m^2/2$: Because the $\cos(2\omega t)$ term cannot swing below extinction (by the definition of extinction), this DC component "lifts" the $\cos(2\omega t)$ term above extinction by exactly ½ of the $\cos(2\omega t)$ magnitude. In an AC coupled system, both this term and $\beta^2$ term are not used.

$\Psi_m^2/2 \cos(2\omega t)$: This term corresponds only to the Faraday modulation angle, $\Psi_m$. It is at double the modulating frequency and is independent of $\beta$. The independence is clear if the output of a bandpass filter centered at frequency $2\omega t$ is observed as $\beta$ is varied.

Now $\Psi_m \cos(\omega t)$ is the electronic signal applied to the optical modulator which provides an optical rotation of $\Psi_m' \cos(\omega t)$. After passing through the sample and the analyzer, the signal is detected (typically with a PIN photodiode and a current-to-voltage operational amplifier). The AC amplifier output is a composite of the two sinusoids: $2\beta\Psi_m'' \cos(\omega t)$ and $\Psi_m''^2/2 \cos(2\omega t)$. The relationship of $\Psi_m$ to $\Psi_m'$ to $\Psi_m''$ is a function of the optical modulator characteristics, the PIN detector, its amplifier, and the feedback resistor (and all their temperature coefficients). But it is important to recognize that all of these influences are common to both frequencies $2\beta\Psi_m \cos(\omega t)$ and $\Psi_m''^2/2 \cos(2\omega t)$. For the remainder of this document, we use $\Psi_m$ alone as both an " input and output variable in place of $\Psi_m'$ or $\Psi_m''$. $\Psi_m$ can be viewed as the carrier for the measured polarization rotation information, $\beta$.

Understanding the Even Frequencies
Repeating Eq.(26)

$I/I_0=(K_0+K_{90})/2-(K_0-K_{90})/2\{J_0(2\Psi_m)\cos 2\beta-2J_1(2\Psi_m)\sin 2\beta\cos(\omega t)$ $-2J_2(2\Psi_m)\cos 2\beta\cos(2\omega t)+2J_3(2\Psi_m)\sin 2\beta\cos(3\omega t) +2J_4(2\Psi_m)\cos 2\beta\cos(4\omega t)-2J_5(2\Psi_m)\sin 2\beta\cos(5\omega t)$ $-2J_6(2\Psi_m)\cos 2\beta\cos(6\omega t)+2J_7(2\Psi_m)\sin 2\beta\cos(7\omega t) +2J_8(2\Psi_m)\cos 2\beta\cos(8\omega t)- \ldots\}$,  Eq.(26)

and recognizing the Bessel relationships, $\cos(2\Psi)=J_0(2\Psi)-2J_2(2\Psi)+2J_4(2\Psi)-2J_6(2\Psi)+2J_8(2\Psi)+ \ldots$  Eq.(41)

$\sin(2\Psi)=2J_1(2\Psi)-2J_3(2\Psi)+2J_5(2\Psi)-2J_7(2\Psi)+ \ldots$,  Eq.(42)

Eq.(41–42) are the sources of the alternating signs of the frequencies in Eq.(27–28). Summing the frequencies according to the Bessel relationships in Eq.(41–42), Eq.(26) can be simplified to a closed form expression, $I/I_0=(K_0+K_{90})/2-(K_0-K_{90})/2\{\cos(2\Psi)\cos(2\beta)-\sin(2\Psi)\sin(2\beta)\}$  Eq.(43)

for $\beta=0$, which eliminates all of the odd frequencies, Eq.(43) reduces to:

$I/I_0=(K_0+K_{90})/2-(K_0-K_{90})/2 \cos(2\Psi)$  Eq.(44)

which is identical to Eq.(6)

Figure 4:
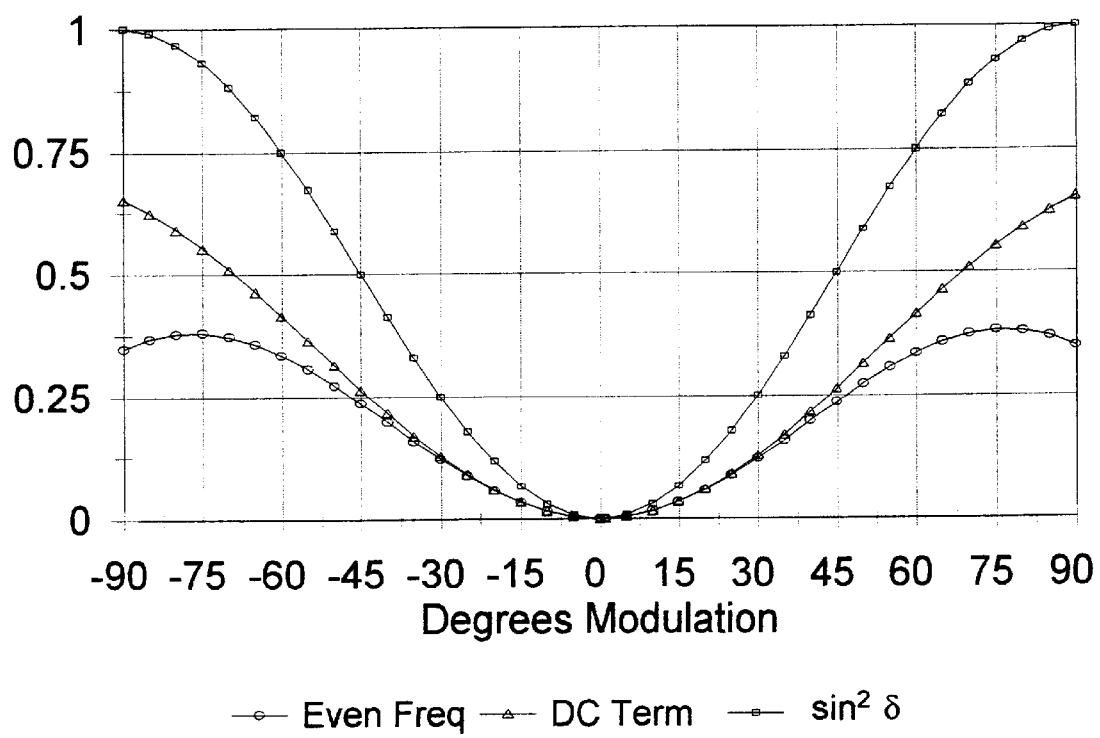
FIG. 4 is a graph showing the distribution of light energy detected at the output of the polarimeter between all even frequencies, the DC term, along with the total energy, $\sin^2 \delta$, for a range of optical modulation.
Figure 5:
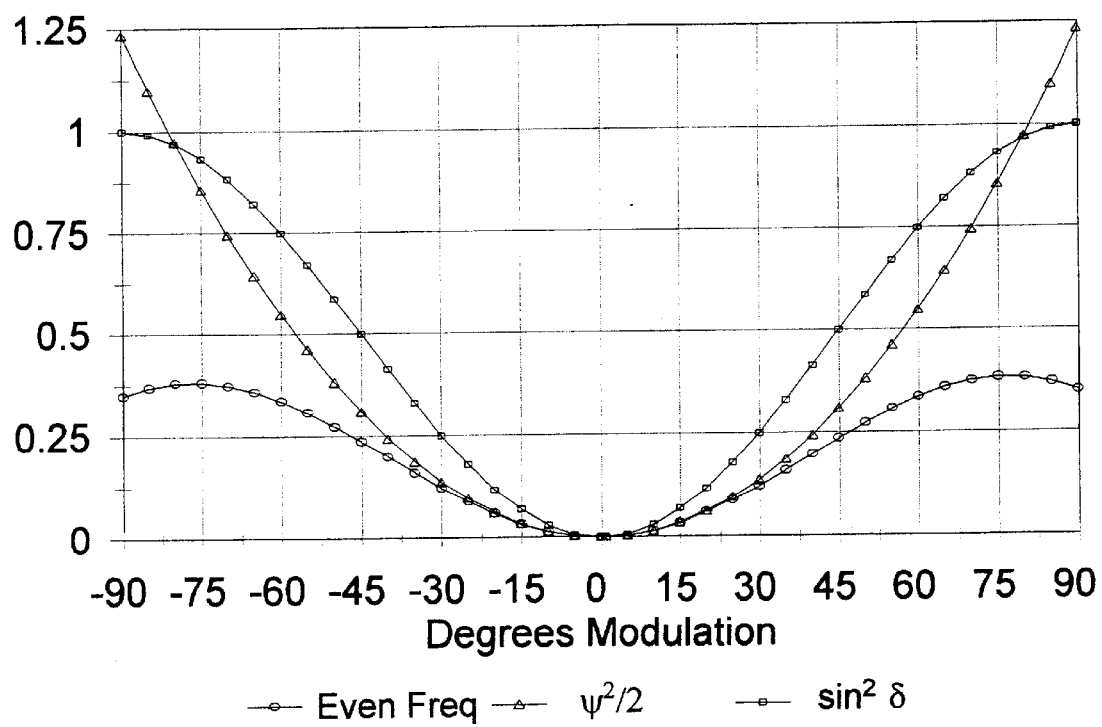
FIG. 5 is a graph depicting the distribution of light energy detected at the output of the polarimeter for even frequencies and Algorithm 2, ($\Psi^2/2$), and the total energy, $\sin^2 \delta$.

$I/I_0=(K_0+K_{90})/2-(K_0-K_{90})/2 \cos(2\delta)$,  Eq.(6)

further, the cos term of Eq.(44) can be described as $\cos(2\delta)=\cos(2\Psi)=J_0(2\Psi)+\Sigma(\text{even frequencies})$ The total light energy, $\cos(2\delta)$, is then equal to the sum of the DC term, $J_0(2\Psi)$, and the even frequencies. FIG. 4 shows how the light is split between the DC term and the even frequencies. FIG. 5 shows Algorithm 2 and the even frequencies, with the DC term eliminated by AC coupling. The computed Algorithm 2 signal, $\Psi_m^2/2$, is equal to the even frequencies for small modulation angles, $\Psi_m$, and then increases for high $\Psi_m$ as the square function overtakes the $\sin^2 \delta$ function. The even frequency energy broad maxima at 77° indicates perhaps a practical modulation limit for these Algorithms.

Figure 6:
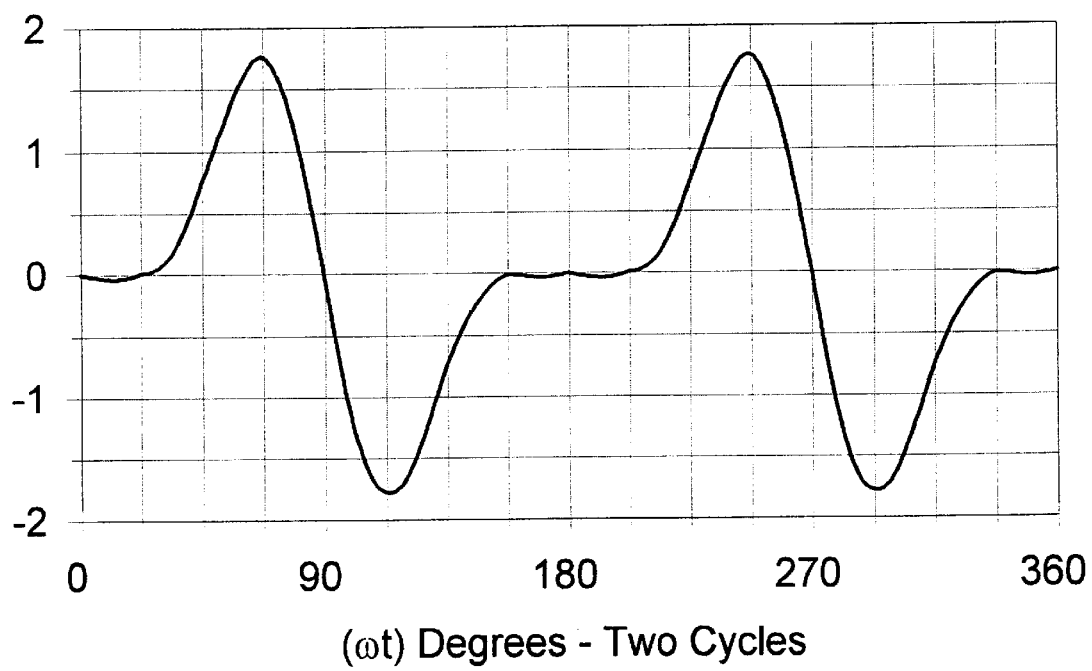
FIG. 6 shows the shape of the waveform of light energy detected at the output of the polarimeter at 75° modulation.

In the previous description of the single series term analysis, the DC component, $\Psi_m^2/2$, "lifts" the composite output waveform above extinction. As the modulation angle $\Psi_m$ increases, the composite output waveform becomes more and more peaked requiring more and more DC component (shown in FIG. 4) to "lift" the waveform above extinction. FIG. 6 shows the composite output waveform containing only even frequencies at 75 degrees modulation.

Understanding the odd frequencies
Repeating Eq.(43), $I/I_0=(K_0+K_{90})/2-(K_0-K_{90})/2\{\cos(2\Psi)\cos(2\beta)-\sin(2\Psi)\sin(2\beta)\}$,  Eq.(43)

the derivative with respect to $\Psi$ is, $dI/d\Psi=I_0(K_0-K_{90})\{\sin(2\Psi)\cos(2\beta)+\cos(2\Psi)\sin(2\beta)\}$.  Eq.(45)

Applying the identities $\sin x \cos y=\frac{1}{2}\{\sin(x+y)+\sin(x-y)\}$  Eq.(46)

$\cos x \sin y=\frac{1}{2}\{\sin(x+y)-\sin(x-y)\}$  Eq.(47)

we get $dI/d\Psi I_0(K_0-K_{90})\sin(2\Psi+2\beta)$  Eq.(48)

Repeating Eq.(30)

$dI/d\delta=I_0(K_0-K_{90})\sin(2\delta)$  Eq.(30)

again for $\beta=0$, Eq.(48) is the same as Eq.(30) showing that the odd frequencies are a derivative function of $\Psi$.

Figure 3:
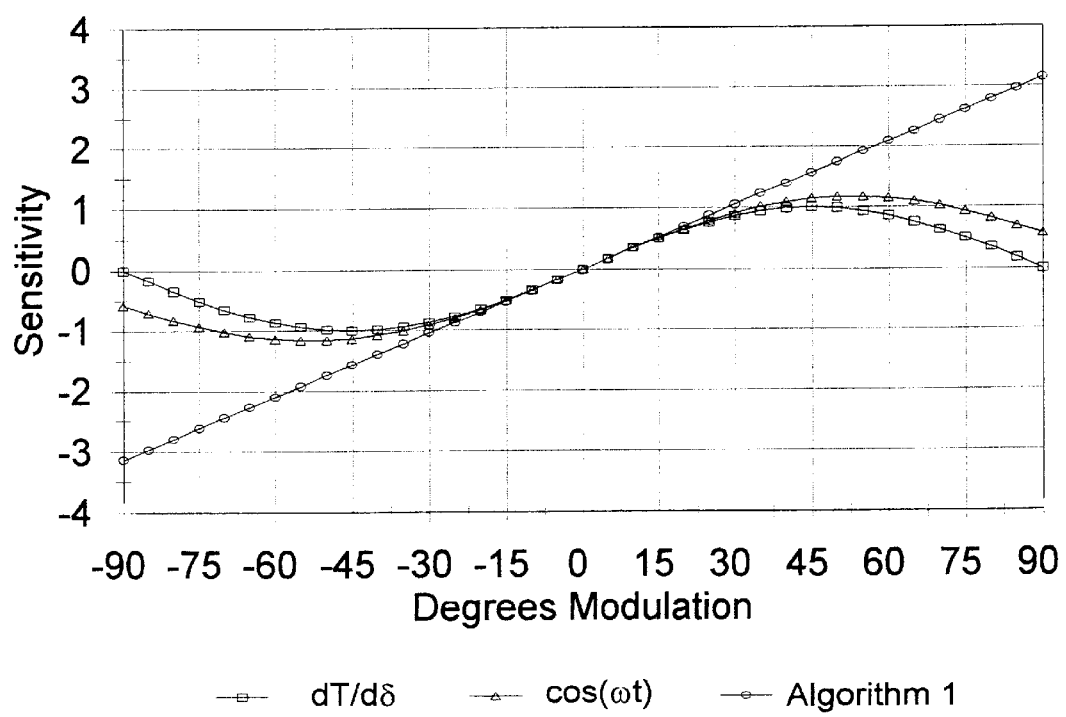
FIG. 3 is a graph comparing the sensitivity of a single frequency lock in amplifier, cos ($\omega t$), the derivative dT/d$\delta$, and Algorithm 1.

FIG. 3 shows a plot of Algorithm 1, the derivative $dI/d\delta$, and the Bessel coefficient $J_1(2\Psi)$ (which peaks at 52.746°). Summing all of the odd frequencies of Eq.(28) yields a curve identical to the first derivative in FIG. 3 with a maximum at 45°. This means that all standard polarimeters, using lock-in amplifiers at a single frequency, $\cos(\omega t)$, are actually traversing a Bessel $J_1(2\Psi)$ curve with a peak at 52.75°, not at 45°. This single frequency $J_1(2\Psi) \cos(\omega t)$ curve is approximately equal to $dI/d\delta$ for small modulation angles.

Standard polarimeters gain very little increase in sensitivity as the modulation angle exceeds about 30° and of course the sensitivity actually begins to decrease at high modulation angles. Now we see from FIG. 3 that by using Algorithm 1, maximum sensitivity is no longer limited to 52.75° but continues to linearly increase beyond 52.75°.

In taking measurements with a polarimeter, we first adjust the instrument to $A_1=0=2\beta\Psi_m$, or $\beta_0=0$. We then insert a sample into the optical path to get a value for the sample, $A_{1S}=2\beta_S\Psi_S$, where the subscript "S" indicates a measurement with a sample. If the initial baseline value is not zero, we cannot get a correct value for $A_{1S}$ by subtracting the nonzero baseline. This is because Algorithm $A_1$ is a derivative, a rate of change signal, and the system gain changes as the initial baseline value moves away from zero. Gillham solved this problem by adding a second Faraday rotator as a compensator in a null feedback loop to insure that all measurements were made at null. As stated earlier, all of the more recent researchers have continued to use a null feedback loop.

Practical Limits of the Algorithms

If we evaluate the coefficients of the odd and even frequencies at maximum $\beta=0.02255°=0.000394$ radians, (for a glucose concentration of 500 mg/dL at 633 nm wavelength and 10 mm path length) and at various modulation angles, we have Table 1, shown below.

Most standard laser diodes have a photodetector integrated with the laser diode that senses the laser intensity at the backside of the device. The photodetector output is used to control the laser diode power supply to provide constant intensity light output. With this standard control system, the intensity specification $I_0$ is approximately 1%.

In a Russian paper by Korolev et al., "Stabilization of the emission amplitude of semiconductor laser diodes", American Institute of Physics, 1990, they use an external electro-optic amplitude modulator with polarizers crossed at 45° as a feedback system. With this system, laser amplitude fluctuations were reduced 25 to 30 db.

In our system, we already have an optical modulator and 90° crossed polarizers, ($\delta=0°$). In addition we already have a signal proportional to intensity: $\Psi_m^2/2$ from Algorithm 2. Rather than directly stabilizing the light intensity fluctuations, if we stabilize $\Psi_m^2/2$, then our Algorithm 1 output signal $\beta$ (from $2\beta\Psi_m$) will be stable. Note that $\Psi_m$ is the carrier for $\beta$. To stabilize $\Psi_m$, we use the reference channel $\Psi_m^2/2$ signal from a two channel optical system as the input to a control system. The control system then varies the amplitude of the optical modulation to compensate for

TABLE 1

| Modulation | | Max β | | | | |
|---|---|---|---|---|---|---|
| Deg | Rad | Radian | $J_1(2\Psi)$ | $-J_3(2\Psi)$ | $J_5(2\Psi)$ | $-J_7(2\Psi)$ |
| 25° | 0.436 | 3.94E−04 | 3.46E−04 | −3.29E−05 | 1.045E−07 | −4.735E−10 |
| | | | 100% | −9.52% | 0.03% | −0.0001% |
| 50° | 0.873 | 3.94E−04 | 6.92E−04 | −2.63E−04 | 3.343E−06 | −6.061E−08 |
| | | | 100% | −38.1% | 0.48% | −0.0088% |
| 75° | 1.309 | 3.94E−04 | 1.037E−03 | −8.89E−04 | 2.54E−05 | −1.036E−06 |
| | | | 100% | −85.7% | 2.45% | −0.1% |
| 90° | 1.571 | 3.94E−04 | 1.245E−03 | −1.14E−03 | 6.32E−05 | −3.71E−06 |
| | | | 100% | −123.4% | 5.07% | −0.298% |
| Deg | Rad | | $J_2(2\Psi)$ | $-J_4(2\Psi)$ | $J_6(2\Psi)$ | $-J_8(2\Psi)$ |
| 25° | 0.436 | | 9.52E−02 | −1.51E−03 | 9.58E−06 | −3.26E−08 |
| | | | 100% | −1.59% | 0.01% | −0.00003% |
| 50° | 0.873 | | 3.81E−01 | −2.41E−02 | 6.13E−04 | −8.342E−06 |
| | | | 100% | −6.35% | 0.161% | −0.002% |
| 75° | 1.309 | | 8.567E−01 | −1.22E−01 | 6.99E−03 | −2.14E−04 |
| | | | 100% | −14.28% | 0.82% | −0.025% |
| 90° | 1.571 | | 1.234 | −2.54E−01 | 2.086E−02 | −9.19E−04 |
| | | | 100% | −20.56% | 1.69% | −0.075% |

In Table 1, the $J_1(2\Psi)$ and $J_2(2\Psi)$ initial terms are normalized to 100% and the higher order terms are scaled to those values. Remembering that we multiply higher frequency magnitudes by 3, 5, and 7 to correct the $J_1(2\Psi)$ magnitude, (4, 9, and 16 to correct the $J_2(2\Psi)$ magnitude), we could have quantization errors when the correction terms greatly exceed the first term. A practical maximum for modulation may be 60° to 75° (75° is also near the maximum light energy point for the even frequencies shown in FIG. 5).

Stabilization

Figure 7:
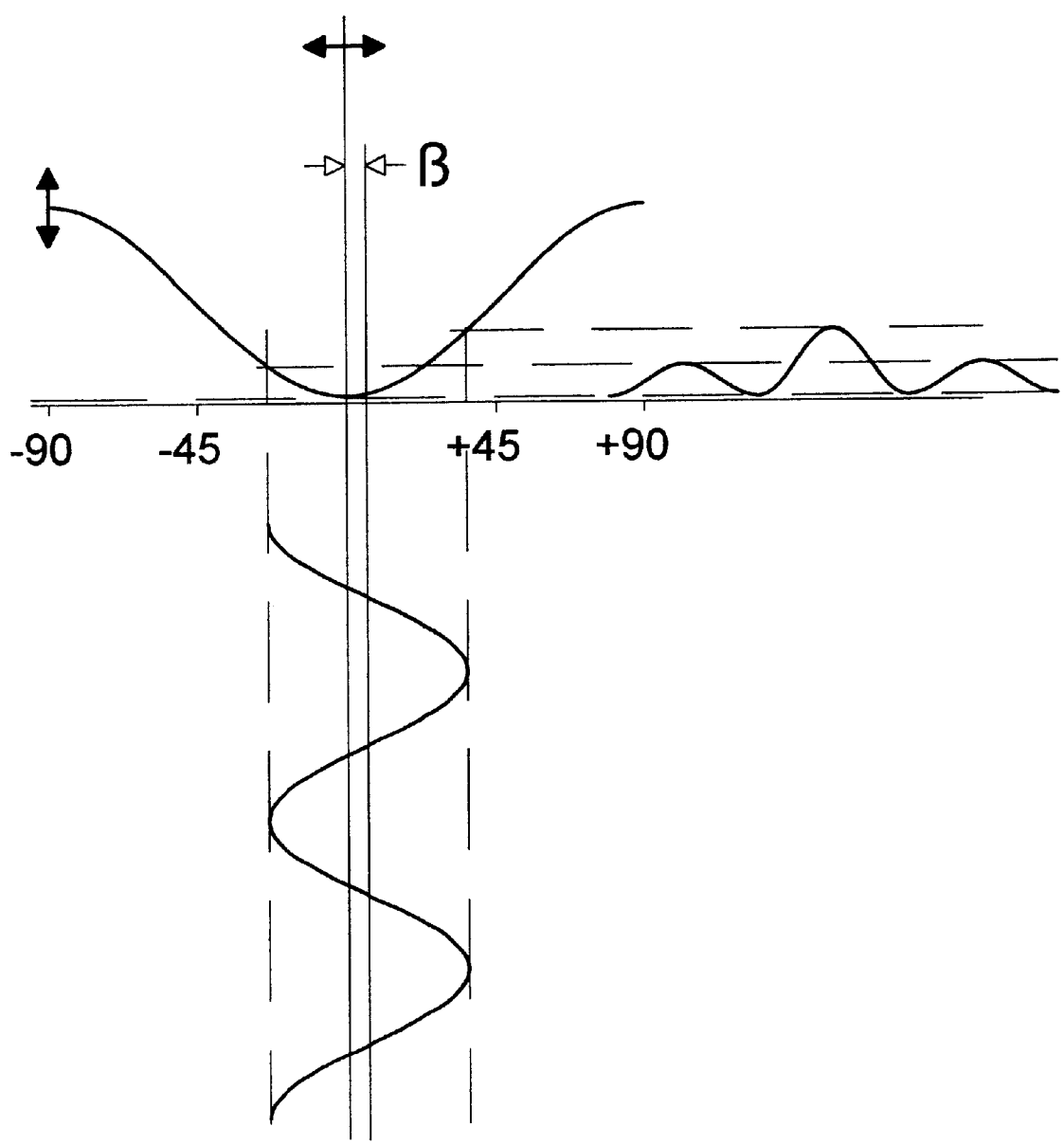
FIG. 7 is similar to FIG. 2 with the addition of sample rotation signal $\beta$, and it also illustrates graphically the optical instabilities that are corrected by feedback loop stabilization methods.

Gillham was correct; sensitivity alone without sufficient precision is not useful. From FIG. 7 we see the output waveform after passing through a sample with rotation $\beta$ ($\beta$ shown by horizontal open arrows, not to scale). It is apparent that the stability of the output signal is dependent upon the stability of the light intensity, $I_0$, through the crossed polarizers (intensity variation is indicated by the vertical double filled arrows on the left side of the plot). It is also clear that variation in the null point, (extinction), also directly affects the output signal $\beta$ (null variation is shown by the horizontal double filled arrows in the center).

changes in light amplitude. This is done by varying the amplitude of the sinusoidal signal driving the optical modulator.

There is a fundamental optical difference between modulation at 0° (our system), and modulation at 45° (Korolev system). A modulator operating at 45° is restricted to small modulation values around 45°. The optical sensitivity of the modulation at 0° is inherently greater and in addition our sensitivity algorithm permits much greater modulation (see FIG. 8). We use the parabolic variable, $\Psi_m^2/2$, instead of the linear variable, $\Psi_m$, as our control signal which also improves our control system sensitivity.

Optical modulators exhibit drift due to various causes. For example, we have observed fluctuations in the null point when modulation current is first applied to a Faraday rotator optical modulator. We believe this is due to temperature induced stress variations in the Faraday glass with the stress causing polarization rotation changes. Similar temperature or mechanically induced polarization changes can occur in any of the optical components. Because of the stress induced drift caused by environmental temperature changes the optical test cell requires close monitoring and adjustments need to be recognized during the course of the measurement series. A stabilized environment and a calibration of test cells is also needed. Because $\Psi_m$ has been stabilized by the intensity feedback loop, we can now use the reference channel $2\beta\Psi_m$ signal for a second feedback system. This loop drives a DC current through the Faraday coil to provide an opposite rotation to the stress induced rotation, thus maintaining our baseline at null, (extinction).

A two channel optical system typically will have two detectors with an analyzer for each. We already have an initial polarizer common to both channels. We depend upon extinction in the measurement channel, but our $\beta$ control system is maintaining extinction only in the reference channel. The analyzers in the two channels will be mechanically adjusted as near as possible to the same null point. However they will never be exactly the same, plus the user may jar the instrument causing a mechanical shift which changes the measure channel zero. Instead of controlling the reference channel signal at zero (extinction), we can introduce an offset in that control system. This offset will be set to force the measurement channel to zero (extinction). This will also give us a means of self checking the instrument: if the offset exceeds some predetermined limit, a message can be displayed that the instrument needs service and calibration.

It may be possible to employ additional electronic signals for the adjustment of the changes that occur in the temperature stress induced changes to the glass measurement cell or to the device proper. The utilization of additional physical structures, ie: filters, phase shift materials or additional constant verdet glass coils and the necessary signal gathering and processing to provide corrective adjustments by current variation or the utilization of mathematical formula to manipulate the data as a correction methods may be feasible.

An alternative method of balancing the two optical channels is to use a compensating Faraday coil in the measurement channel. It can be used to zero, or null, the measure channel prior to inserting a sample, or it can be used in the null feedback loop described by Gillham.

For a given Faraday material, both the Verdet constant and the temperature coefficient of the Verdet constant are known. By measuring the temperature of the compensating Faraday element, we can accurately control the current in the Faraday coil to provide a very precise rotation of the polarized light in the measure channel. This is then used as a calibration factor for the instrument for that specific measurement.

We have seen references by other researchers (our experience also) to letting the system "warm up" for a period of time before taking data. Both intensity and $\beta$ fluctuations are fundamentally thermal processes that start at <5 Hz and progress over a long period of time to <0.01 Hz. We need to take readings in less than 1 minute after initial power on thus making stabilization control systems a critical element of a practical instrument.

Application of the Algorithms and Stabilization Methods to a Non Invasive Glucose Instrument Sensitivity Gillham first recommended 3° as a modulation angle. Several more recent researchers used 3° modulation ("Noninvasive Glucose Monitoring of the Aqueous Humor of the Eye: Part1. Measurement of Very Small Optical Rotations", B. Rabinovitch, W. F. March, R. L. Adams, Diabetes Care, May–June, 1982.); 3° modulation ("Microdegree Polarimetry using a Diode Laser for Glucose Detection", M. J. Goetz, M. D. Fox, R. B. Northrop, IEEE 0-7803-0902, 1992); and 1° modulation ("Noninvasive Glucose Sensing Utilizing a Digital Closed-loop Polarimetric Approach", B. D. Cameron, G. L. Coté, IEEE 0018-9294, 1997).

Gillham was the first to propose and use a Faraday coil as a compensator in a closed loop feedback system. The feedback system removes the rotation of the sample and continually operates at a null point (extinction). The value of the sample rotation then is the DC current required to return to null.

Rabinovitch similarly used Gillham's feedback compensator method with the statement that "higher sensitivity is achieved if the method is made to be null-point, dependent on a feedback mechanism." Likewise, Goetz and Cote used feedback systems to null. A null feedback system acts to minimize the rate of change of sensitivity ($d^2I/d\delta^2$), however it does not maximize sensitivity.

Figure 10A:
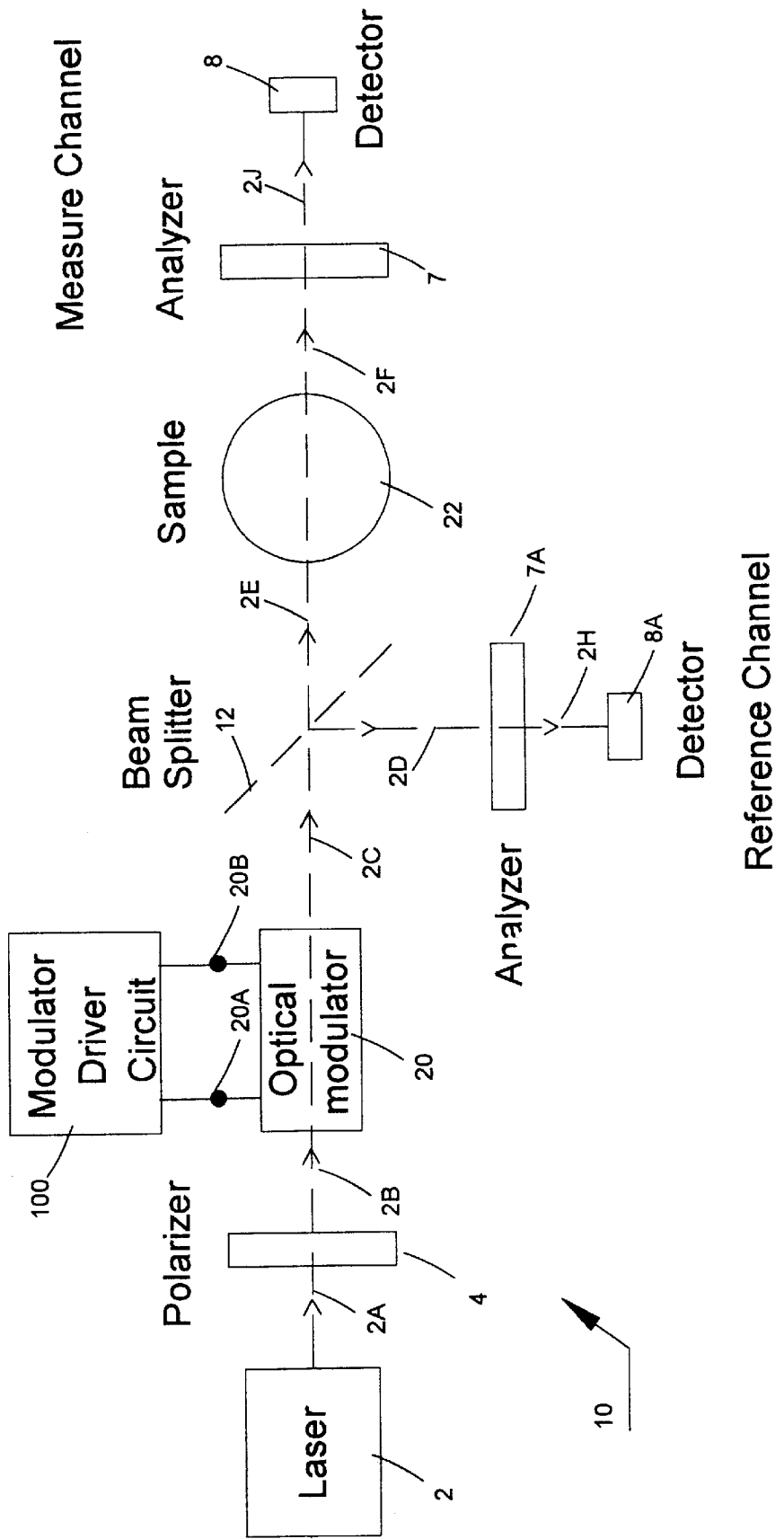
FIG. 10A is a simplified optics diagram of a presently preferred polarimeter system of the invention.
Figure 14:
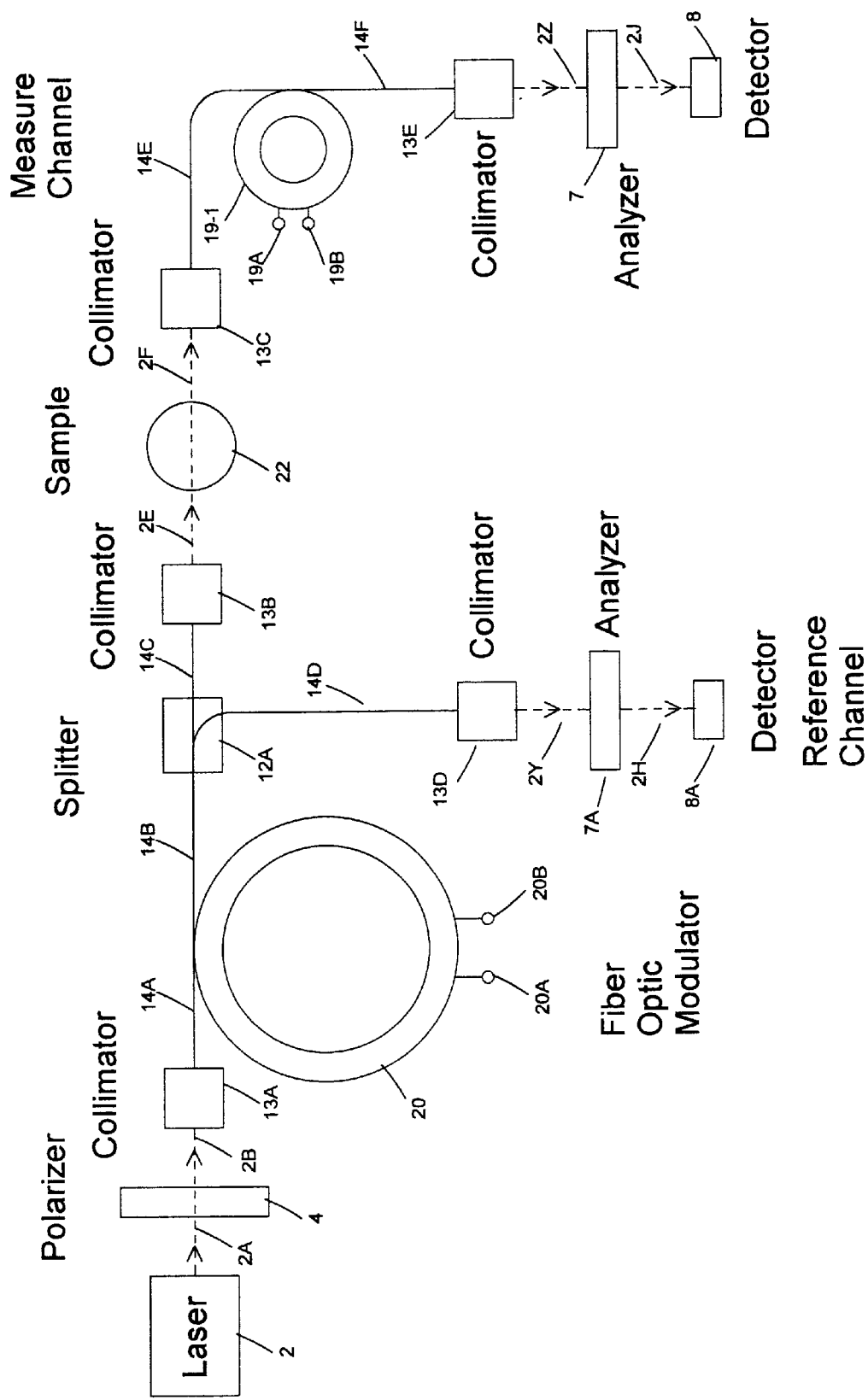
FIG. 14 is an optical diagram of an alternative embodiment to that shown in FIG. 10B.

However, by using the Algorithms developed above, and by optically modulating between 60° and 75°, we can increase sensitivity by 20 to 25 times what other researchers have achieved. As noted above, human tissue with a path length of less than 4 mm (including skin), reduces the glucose rotation angle signal by more than 95%, due to scattering. Thus, we have sufficient sensitivity to make this measurement. It is important to recognize that the level of modulation as indicated above is in excess of that needed for measurement in transparent human tissue. I.e. the anterior chamber of the eye which is primarily comprised of aqueous humor. Aqueous humor is comprised of substances which do not have the properties of, say for instance, skin which our and other researchers have demonstrated scattering and absorption problems. The lack of defined structures, red blood cells and platelets provide for this site as a currently preferred measurement location. Since the eye is transparent, modulation levels of less than 1 degree to approximately 5 degrees should be adequate for "eye" measurements, in which the human eye is the sample 22 as shown in FIGS. 10A, 10B, and 14. As the transparency of the sample decreases, high modulation levels are needed to achieve the necessary signal strength for accurate measurements.

Signal vs. Noise

The preferred embodiment for our signal processing is a digital signal processor (DSP) implementing a Fast Fourier Transform (FFT) which calculates the magnitudes of all of the frequency components of our signal. Instead of an FFT, model-based spectral analysis (MBSA) could be used which has the advantage of shorter sampling times for the same frequency resolution. (An alternative implementation would use bandpass filters for each of the frequencies with precision rectifiers to derive magnitude data. This would require 10 to 20 times the number of I.C.'s and 10 to 20 times the cost of a DSP implementation.)

Increasing the size (i.e., number of bins) of the FFT, (64,128,256, . . . ) increases the selectivity for each of the frequency bins, thereby reducing noise. The signal to noise ratio increases by 3 db each time the size of the FFT is doubled. A practical DSP for this application would be limited by computation speed to a 256 or 512 FFT.

Because the same DSP will generate the modulation sinusoidal signal and time the input A/D data sampling, we can insure that we have a signal sampling interval exactly equal to an integer number of samples per cycle of the signal at our photodetectors. Further, because all of the frequencies that we need to analyze are integer harmonics of our modulation frequency, they will all have an integer number of cycles in our sampling period. This is the ideal case for FFT analysis as there is no 'leakage' of data from one bin to another.

Instead of just increasing the size of the FFT, which is limited by computational power, we can average FFT's. This method of coherent averaging has the same requirement as above: the phase of the sampled input signal must be the same at the beginning of each measured sample set. Coherent averaging then preserves the amplitude of signals that are synchronous (coherent), while reducing the variance of the noise. We can realize a signal-to-noise improvement proportional to the square root of the number of FFT's averaged (see "Understanding Digital Signal Processing", Richard G. Lyons, Addison-Wesley, 1997).

Recognizing the synchronous nature of the output signals of our polarimeter and using these methods of digital signal processing we can noninvasively detect the polarized light rotation of glucose in human tissue even with 95% signal loss due to scattering and absorption.

Referring now to FIG. 10A, a presently preferred embodiment of the optics portion of the noninvasive glucose measurement system of the present invention is designated by numeral 10. Optic system 10 includes a laser 2, which can be a laser producing light in the 750 to 900 nanometer range in which human tissue has minimum absorption. (Additionally, visible lasers in the 600–700 nm range could be used in transparent tissue such as the anterior chamber of the eye.) Laser 2 produces a beam 2A that passes through a first polarizer 4. The polarized beam 2B emanating from polarizer 4 passes through an optical modulator 20, which presently is preferred to be a Faraday rotator. It is important to recognize that the utilization of other methods and effects may be utilized in the conceptual approach such as voltage other than current, phase shift as apposed to angular measurements and other materials such as PLZT other than Faraday glass.

For example, there are several devices that can serve as the optical modulator 20. A Faraday rotator is one such device. A solid state Kerr cell could also be used as an optical modulator. A Kerr cell is a system in which the electric field is applied transversely to the propagating light beam. The medium of the Kerr cell can range from liquids, such as nitrobenzene, to crystalline materials, such as KDP (potassium di-hydrogen sulfate) or amorphous solids, such as PLZT (lead lanthanum zirconate-titanate). A Pockels cell, in which the electric field is applied along the propagation direction in an appropriate crystalline medium, again such as KDP, could also be used as an optical modulator.

Figure 11A:
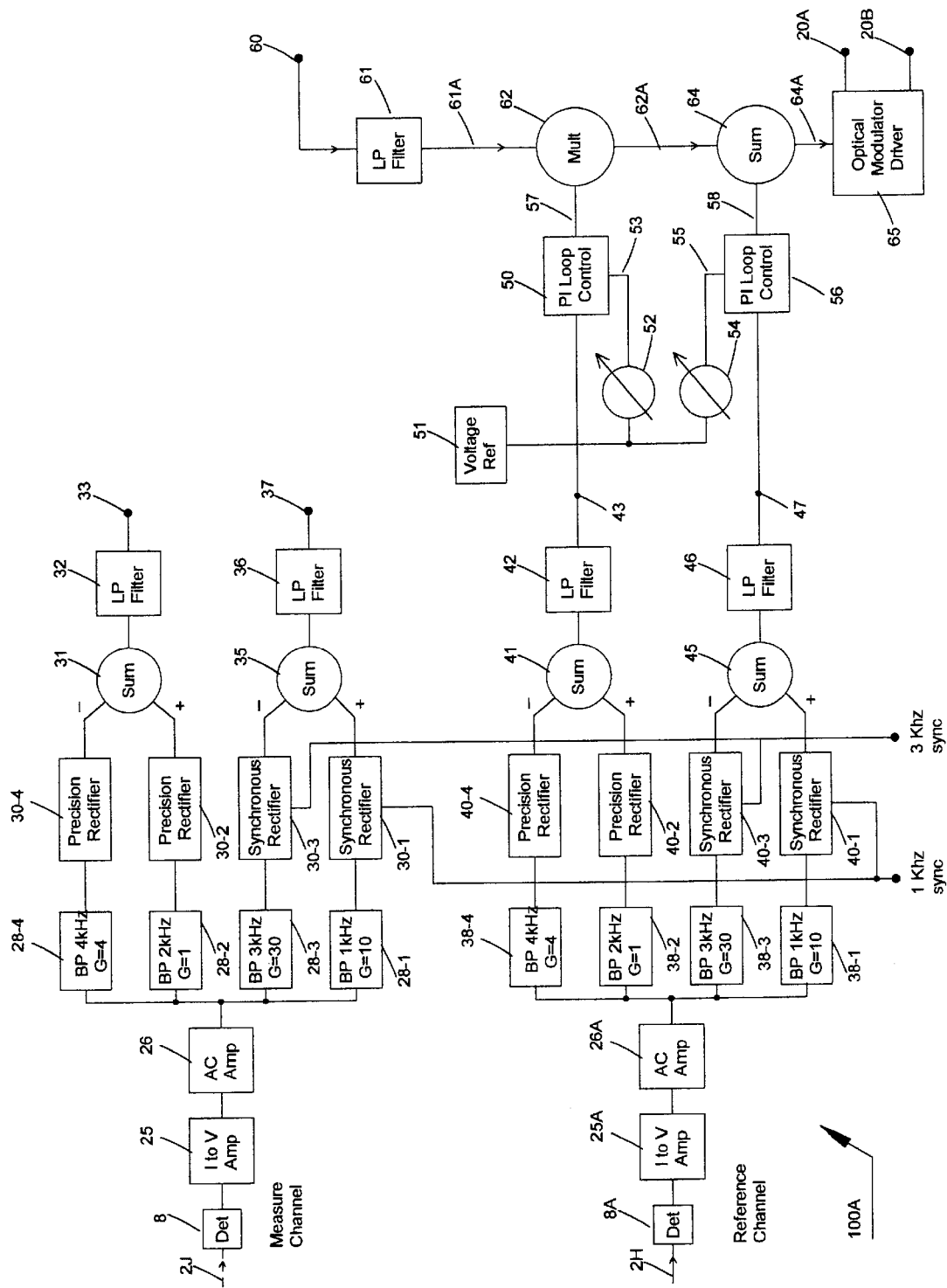
FIG. 11A is a block diagram of an analog implementation of the present invention.
Figure 12:
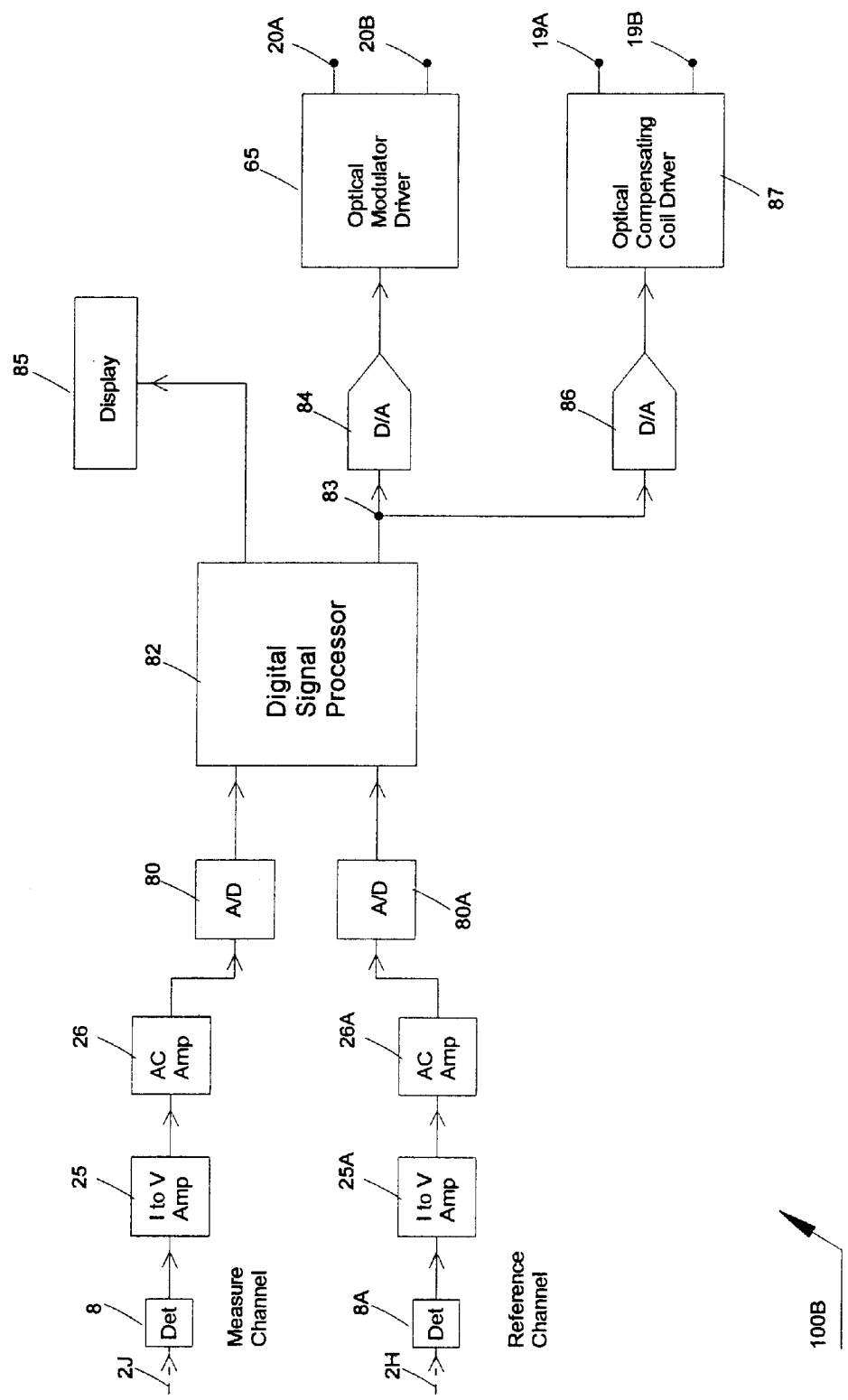
FIG. 12 is a block diagram of a frequency domain implementation using a digital signal processor (DSP) of the present invention.

Optical modulator 20 has two terminals 20A and 20B which receive a modulating current produced by the circuitry 100A shown in FIG. 11A or the circuitry 100B shown in FIG. 12. The modulated laser beam 2C emanating from Faraday rotator 20 impinges on a non-polarizing beam splitter 12 transmitting a beam 2E and reflecting a beam 2D. Beam 2D passes through a second analyzer 7A and emerges therefrom as a beam 2H which then impinges on a first detector 8A. (Polarizer 4 and analyzers 7 and 7A can be polarizers which have a high extinction ratio, such as POLAROID sheet polarizer HN22 or CORNING POLARCOR polarizer.) The transmitted beam 2E passes through an in situ human tissue sample 22 such as an ear lobe, or eye if present, and emerges from the sample as beam 2F which passes through a third analyzer 7 as beam 2J, which impinges on a second detector 8.

FIGS. 10B and 10C show a preferred, more detailed implementation of the polarimeter system of FIG. 10A. The portion including laser 2, polarizer 4, optical modulator 20, and beam splitter 12 are the same as in FIG. 10A. Similarly, beam 2C in FIG. 10B is reflected by beam splitter 12 to provide beam 2D which passes through analyzer 7A as shown in FIG. 10B to produce beam 2H, which impinges on reference channel detector 8A.

However, as shown in FIGS. 10B and 10C, glass element 18 incorporating complementary reflections to cancel reflection-induced distortions in the optical rotation and having a known temperature-dependant Verdet constant is used as electro-optic control element to guide the light of the measurement channel through analyzer 7. Beam 2F in FIG. 10B emanates from sample 22 in the measurement channel and is reflected by inclined surface 18A of glass guide 18 to produce beam 2V, which is guided to inclined surface 18B to produce beam 2Z. Beam 2Z passes through analyzer 7B to produce beam 2J, which impinges on detector 8 of the measurement channel. A compensating coil 19 is used to zero the measurement channel electronically, by driving compensating coil 19 so as to produce extinction of the laser beam passed by the crossed polarizers with no sample in its measurement path.

The temperature of the glass guide 18 is measured by means of a temperature sensor 21 (FIG. 10B), the output 21A of which is amplified and used to adjust the current supplied to compensating coil 19 according to the temperature coefficient of the Verdet constant of the glass guide 18. As shown in subsequently described FIG. 12, the analog output produced on conductor 21A by temperature sensor 21 can be digitized by an A/D converter 21B and supplied as a digital input to digital signal processor 82, which takes into account the temperature of glass guide 18 in computing the amount of drive current to be supplied by optical compensating coil driver 87 to the terminals 19A and 19B of compensating coil 19. Because the temperature coefficient of the Verdet constant is linear, compensation is accomplished by applying the slope of the temperature coefficient to the measured temperature and then correcting the current applied to the coil around the Faraday glass so that the rotation of the polarized light remains constant with temperature changes. By maintaining this constant rotation of the polarized light, we have a method of calibrating the entire instrument every time it is powered on. The simple approach of a look up table is adequate in this instance. However, development of appropriate algorithms may be included in the eventual design upon determination of device components and identification of targeted measurement bands or results.

The use of glass element 18 in the measurement channel allows use of a smaller and more convenient mechanical design to measure glucose concentration in the human body. (See FIG. 15.) The inclined surfaces 18A and 18B of glass guide 18 are inclined at 45 degrees relative to the beam 2V and, using a known technique, are rotated 90 degrees relative to each other about the measurement beam path so as to provide complementary reflections that cancel the 5 distortions of the optical rotation resulting from the two reflections from inclined surfaces 18A and 18B. The use of glass element 18 and compensation coil 19 in the measurement path also allows calibration of the polarimeter with no sample present in the measurement path. This is accomplished by providing a precise known current (for example, one generated from a reference source) through compensation coil 19. That causes a certain amount of rotation of the light passing through glass guide 18, and a calibration number representative of that amount of rotation can be produced in response to the detector output and stored as a calibration number. The stored calibration number then can be used every time a measurement of a sample is made to determine the amount of rotation caused by the sample.

A single Faraday glass element with integral complementary reflections is not required for the function described above; two separate mirrors incorporating complementary reflections and a separate Faraday glass compensation element can be an alternate implementation. Either metal or dielectric mirrors can be used.

In accordance with the present invention, the circuitry required, in effect, to stabilize the physical components shown in FIG. 10A and to implement Algorithms 1 and 2 can be provided as an analog circuit including various bandpass filters required for each of the terms in Eq.(28) or by the "frequency domain" circuit of FIG. 12 including a digital signal processor (DSP) which computes Fast Fourier Transforms (FFTs) to obtain the frequency coefficients represented in above Algorithm 1 and Algorithm 2 to obtain $\beta_m$.

Figure 11B:
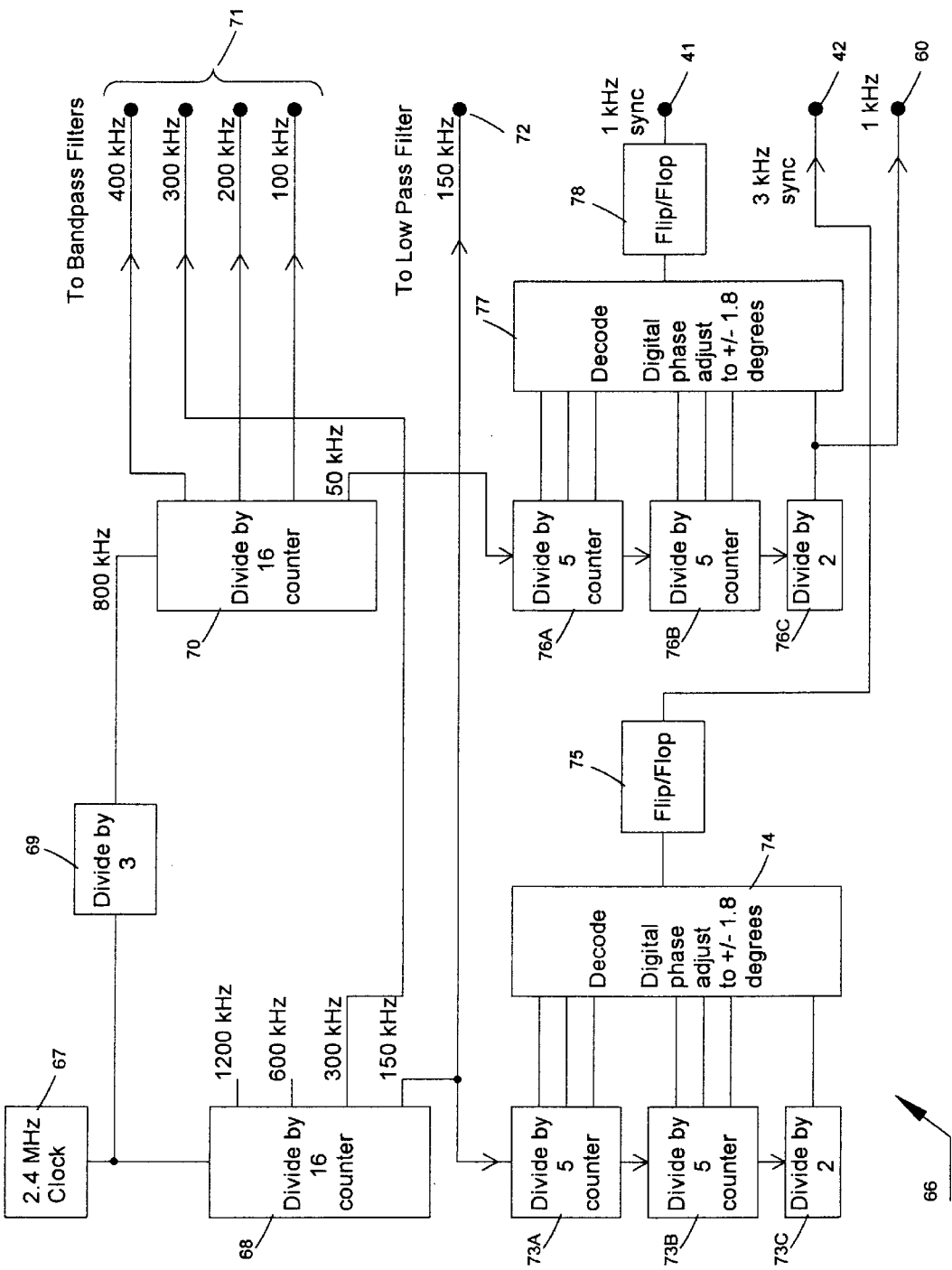
FIG. 11B is a block diagram of digital circuitry for producing the digital signals required as inputs to the system shown in FIG. 11A.

Referring next to FIG. 11A, time domain modulation circuit 100A includes first detector 8 and second detector 8A previously shown in FIG. 11. Each detector can be a PIN diode such as a HAMAMATSU 55821-0 silicon PIN photodiode. Current through first PIN detector diode 8 is connected to the summing input of a current-to-voltage amplifier 25, which preferably is an operational amplifier having a FET input stage, such as an LT1113 low noise dual JFET op amp, available from Linear Technology Corporation (LTC). The output of amplifier 25 is connected to the input of an AC coupled amplifier 26, which can be one half of an LT1013 op amp from Linear Technology Corporation. The output of AC amplifier 26 is connected to the inputs of four bandpass filters 28-1, 28-2, 28-3, and 28-4. Bandpass filter 28-1 has a gain of 10 a center frequency of 1 kilohertz. Bandpass filter 28-2 has a gain of 1 and a center frequency of 2 kilohertz. Bandpass filter 28-3 has a gain of 30, thereby implementing the 3×multiplication for Algorithm 1, and a center frequency of 3 kilohertz. Bandpass filter 28-4 has a gain of 4, thereby implementing the 4×multiplication of Algorithm 2, and a center frequency of 4 kilohertz. Each of bandpass filters 28-1,2,3,4 can be a LTC1164-8 switched capacitor or 8 pole bandpass filter. These bandpass filters are respectively clocked by the four signals 71 shown in FIG. 11B, wherein each bandpass filter is clocked at a frequency 100 times its center frequency.

The outputs of bandpass filters 28-2 and 28-4 are connected to inputs of conventional full wave precision rectifiers 30-2 and 30-4, respectively. The outputs of precision rectifiers 30-2 and 30-4 are connected to the (+) and (−) inputs of an analog summing amplifier 31, which can be an LT1014 op amp from LTC. The LT1014 op amp together with a feedback capacitor also form low pass filter 32. The output of low pass filter 32 is connected to conductor 33, and produces a signal $\Psi_m^2/2$, which is Algorithm 2. The outputs of bandpass filters 28-1 and 28-3 are connected to inputs of synchronous rectifiers 30-1 and 30-3, respectively.

Synchronous rectifiers 30-1 and 30-3 can be implemented by means of a CD74HCT4053 triple SPDT analog switch from Harris Semiconductor and two LT1014 op amps from LTC, operated to provide a gain of +1 or −1. The rectification is done according to the 1 kHz and 3 kHz digital sync signals rather than at the zero crossing points of the rectified signals. The output of synchronous rectifier 30-1 is connected to the (+) input of summing amplifier 35, and the output of synchronous rectifier 30-3 is connected to the (−) input of summing amplifier 35, which is identical to summing amplifier 31. The output of summing amplifier 35 is connected to the input of low pass filter 36, which is identical to low pass filter 32. The output of low pass filter 36 is connected to conductor 37, on which the signal $2\beta_m\Psi_m$, which is Algorithm 1, is produced. Synchronous rectifier 30-1 is clocked by a 1 kilohertz digital sync signal on conductor 41. Synchronous rectifier 30-3 is clocked by a 3 kilohertz digital sync signal on conductor 42.

Similarly, the second PIN detector diode 8A produces a current representative of the reference channel beam 2H of FIG. 10A, which is converted to a voltage by current-to-voltage amplifier 25A and is separated from its DC components by AC amplifier 26A, the output of which is connected to the inputs of bandpass filters 38-1, 2, 3, and 4 (which are identical to above described bandpass filters 28-1, 2, 3, 4, respectively). Synchronous rectifiers 30-1 and 30-3 and precision rectifiers 30-2 and 30-4 are "repeated" as synchronous rectifiers 40-1 and 40-3 and precision rectifiers 40-2 and 40-4 connected as shown. Connections of summing amplifiers 41 and 45 are identical to those of previously described summing amplifiers 31 and 35.

The connections of low pass filters 42 and 46 are identical to the connections of low pass filters 32 and 36, respectively. However, the output of low pass filter 42 produces a signal $\Psi_R^2/2$ on conductor 43, which is connected to the input of a PI (proportional, integral) loop control circuit 50, which can be implemented as an LT1013 op amp with an input resistor and a feedback loop including a capacitor in series with a resistor. If a derivative function is needed, it can be easily implemented with the same op amp and additional resistors/capacitors. Another input of PI loop control circuit 50 is connected by conductor 53 to a first potentiometer 52, which produces a stable, selectable voltage on conductor 53. The voltage on conductor 53 is divided down from a reference voltage $V_{REF}$ produced by a stable voltage reference circuit 51. The output of PI loop control circuit 50 on conductor 57 is applied to the (+) input of an analog multiplier circuit 62, the other input of which is connected by conductor 61A to the output of a low pass filter 61. Analog multiplier 62 can be an AD633 available from Analog Devices, Inc. Potentiometer 52 can be adjusted to set the magnitude of the AC modulating signal applied to terminals 20A and 20B of optical modulator 20.

The input to low pass filter 61 is connected to conductor 60, which receives a 1 kilohertz squarewave signal from the digital logic circuitry 66 of FIG. 11C. Low pass filter 61 is an 8 pole switched capacitor filter having a frequency of between 1.2 and 1.5 times the 1 kHz fundamental frequency applied to conductor 60, and can be an LTC1069-1, commercially available from Linear Technology Corporation. Since the first harmonic of a 1 kHz squarewave is at 3 kHz, the output of low pass filter 61 is a sine wave at 1 kHz, by rejecting all higher harmonics.

Figure 2:
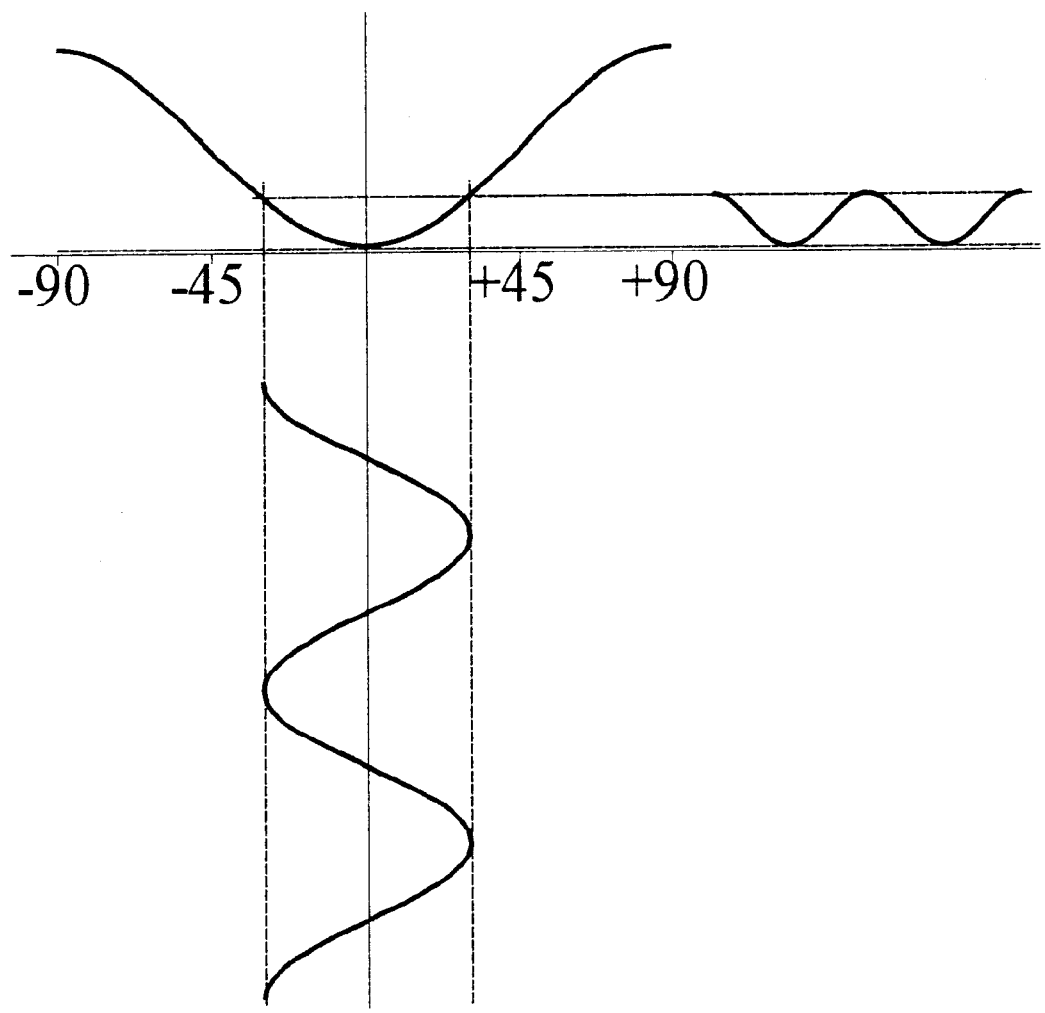
FIG. 2 shows a modulating sinusoidal signal applied to the $\sin^2 \delta$ curve of 90° crossed polarizers; also shown is the resulting doubled frequency output signal.

The output of low pass filter 46 produces the signal $2\beta_R\Psi_R$ on conductor 47, which is connected to the input of a second PI loop control circuit 56 that is identical to first PI loop control circuit 50. A second input of PI loop control circuit 56 is connected by conductor 55 to a second potentiometer 54, which produces a second reference voltage on conductor 55 based on the reference voltage $V_{REF}$ produced by reference voltage circuit 51. The output of second PI loop control circuit 56 is connected by conductor 58 to one input of an analog summing circuit 64, the other input of which is connected by conductor 62A to the output of multiplier 62. The output of summing circuit 64 is connected by conductor 64A to the input of a power amplifier 65, the outputs of which are connected to conductors 20A and 20B of optical modulator 20 of FIG. 2. Potentiometer 54 can be adjusted to provide an offset to compensate for differences between the measurement channel circuitry and the reference channel circuitry. This is accomplished by adjusting reference channel potentiometer 54 to adjust extinction of the measurement channel before sample 22 is introduced.

The digital circuitry required to produce signals 71 and 72 (FIG. 11B) for the bandpass filters and low pass filters in FIG. 11A is straightforward, but is shown in FIG. 11B for completeness. A crystal clock circuit 67 produces a 2.4 megahertz clock signal applied to the divide by 16 counter 68, which produces four output signals of frequencies 150, 300, 600, and 1200 kilohertz as shown. The 300 kilohertz signal provides one of the bandpass filter clocking signals 71. The 2.4 megahertz clock signal is divided by 3 by divider 69 to produce the 800 kilohertz signal that is input to a divide by sixteen counter 70, which produces 50 kilohertz, 100 kilohertz, 200 kilohertz and 400 kilohertz signals as shown. The 100, 200, 300 and 400 kilohertz clock signals are connected to provide the center frequencies of the above mentioned bandpass filters.

The 150 kilohertz output of counter 68 is applied to an input of divide-by-five counter 73A, the MSB output of which is connected to the input of divide-by-five counter 73B, the MSB output of which is connected to the input of divide by two counter 73C.

The outputs of the three counters 73A, B, and C are decoded by a decoder circuit 74, the inputs of which can be adjusted by suitable jumper switches to allow digital phase adjustment of the output signal applied to an input of flip-flop 75 in increments of ±1.8°. The output of flip-flop 75 is connected to conductor 42 and provides the 3 kilohertz digital sync signal required by the circuit of FIG. 11A. The 50 kilohertz output of divide-by-sixteen counter 70 is applied to an identical sequence of counters 76A, B, and C, the outputs of which are decoded by a decoder 77 identical to decoder 74 to produce an output applied to the input of flip-flop 78, wherein the phase of output decoder 77 can be adjusted in increments of ±1.8°. The output of flip-flop 78 is connected to conductor 41 to produce the above mentioned 1 kilohertz digital sync signal.

Digital Signal Processor Implementation

Referring next to FIG. 12, a frequency domain implementation 100B of the optical modulator driver circuit includes above-described PIN diodes 8 and 8A and their associated current-to-voltage amplifiers and AC amplifiers are shown. The measurement channel includes an analog-to-digital converter 80 having its input connected to the output of AC amplifier 26 and its output connected to a digital data bus of a DSP integrated circuit 82, which can be a TMS 320VC33 32-bit floating point DSP, from Texas Instruments. Similarly, the reference channel includes an analog-to-digital converter 80A having its input connected to the output of AC amplifier 26A and having its digital output connected to the digital bus 83 of DSP 82. The digital bus 83 of DSP 82 is connected to the input of a digital-to-analog converter 84. The analog output of digital-to-analog converter 84 is connected to the input of power amplifier 65. DSP 82 also is connected to a display 85.

Digital bus 83 also can be connected to the digital input of the second digital-to-analog converter 86, the analog output of which produces a DC drive to an optical compensating coil driver circuit 87 the outputs of which are connected to terminals 19A and 19B of compensating coil 19 of FIG. 10B, if that feature is used. If compensating coil 19 is used, it can be controlled by digital signal processor 82 to provide a value of the DC drive sufficient to zero the measurement channel.

According to the present invention the frequency domain implementation of the polarimetry instrument is the most preferred embodiment, because it can be implemented using only about a half dozen integrated circuits, in contrast to the approach of FIGS. 11A and 11B, which requires more than forty integrated circuits to provide an implementation of only the first four frequency terms of Eq.(28).

For DSP 82 to derive suitable values of $\Psi_m$ and $\beta_m$ to accurately implement the first four frequency terms of equation 28, FFTs of "size" 128 to 512 are preferred. Analog-to-digital converters 80 and 80A can be 50 kilohertz devices, having a digital word width of 16–24 bits. Analog-to-digital converters 80 and 80A need to sample the analog inputs at twice the highest frequency of the highest harmonic that is needed, according to the Nyquist requirement.

Figure 13:
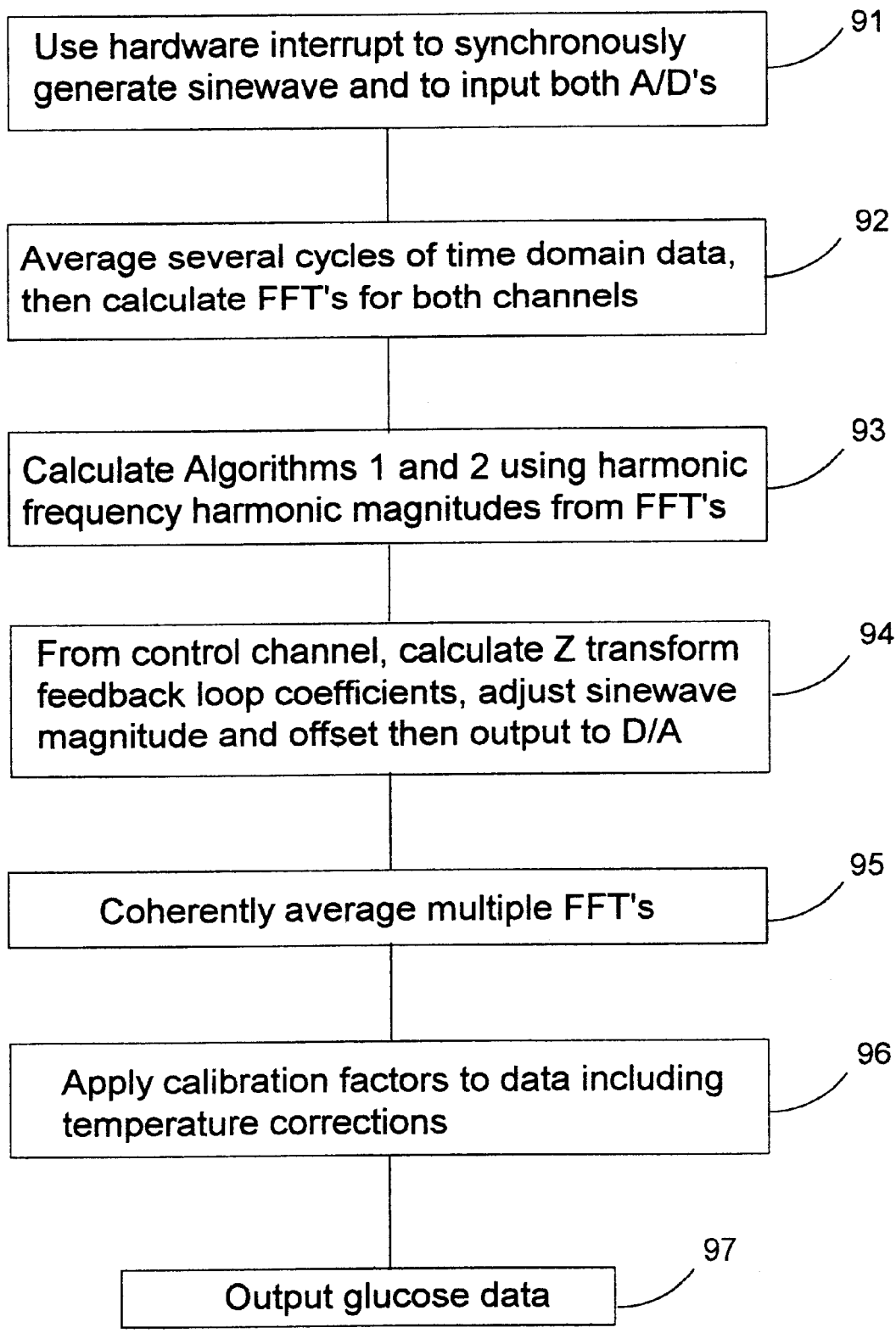
FIG. 13 is a flow chart of the operation of the digital signal processor in the diagram of FIG. 12.

Referring to the flow chart of FIG. 13, DSP 82 first collects digital data from both analog-to-digital converter 80 of the measurement channel and analog-to-digital converter 80A of the reference channel and synchronously generates sine wave data on digital bus 83 which is sampled by the input of digital-to-analog converter 84. The hardware interrupt of DSP 82 is clocked every 8 µs to synchronously generate the 1024 Hz sine wave data and to sample analog-to-digital converters 80 and 80A every 32 µs.

Then DSP 82 goes to block 92 of the flow chart of FIG. 13 and inputs time domain data from analog-to-digital converters 80 and 80A, and then computes FFTs every millisecond for both the measurement channel and the reference channel, using commercially available software that can be downloaded from Texas Instruments' web site, File: CZCX0032.ASM, entitled "132 Point DIT Rasix-2, Complex FFT", to compute the FFTs.

The FFT algorithm transforms the output data from analog-to-digital converters 80 and 80A into amplitudes of each harmonic, i.e., into the frequency domain. Thus, DSP 82 goes to block 93 of the flow chart of FIG. 13 and computes the values produced by Algorithm 1 and Algorithm 2, using the frequency harmonic magnitudes from the FFT frequency bins to obtain values of $\Psi_m^2/2$, $\Psi_R^2/2$, $2\beta_m\Psi_m$, and $2\beta_R\Psi_R$. The FFT bins can be considered to be analogous to the precision rectifier outputs of FIG. 11A, which then are summed and filtered to provide the $\Psi_m^2$ and $2\beta_m\Psi_m$ terms.

Next, the operating program of DSP 82 goes to block 94 of the flow chart and computes Z transform feedback loop coefficients to, in effect, simulate the operation of PI loop control circuits 50 and 56 of FIG. 11A. The Z transform is a well known technique which can be used in implementing a control loop in digital form, and permits DSP 82 to adjust the loop coefficients to provide the needed loop stability. The output of the two loops are input to a digital multiplier simulated by DSP 82, one being provided to a multiplication function analogous to block 62 of FIG. 11A and the other being input to a summing function analogous to summer 64 of FIG. 11A. The sine wave generated in block 1 of FIG. 13 then is multiplied by the output of the first simulated control loop and the results are added to the output of the second simulated control loop to adjust the sine wave magnitude and offset and then output the sine wave data to the digital-to-analog converter 84, providing the stabilized digital data representing the desired optical modulator input. The operations of blocks 92, 93, and 94 are performed every 8 to 10 milliseconds, i.e., roughly a hundred times per second.

Next, DSP 82 goes to block 95 of FIG. 13 and coherently averages a number of FFTs in order to increase the signal-to-noise ratio as previously explained.

Then DSP 82 goes to block 96 and applies suitable calibration factors for a particular patient which may be needed to calibrate the raw data and make suitable temperature compensation adjustments as necessary. In block 97 of FIG. 13, the difference in rotation ($\beta_S - \beta_0$) then is converted to a glucose level in the patient's tissue and displayed in a suitable digital display.

FIG. 14 shows an alternate implementation of the optics shown in FIG. 10B, wherein the beam 2B from polarizer 4 is collimated by a collimator 13A and then introduced into an optical fiber 14A. Fiber 14A is wrapped around a torus to form a fiber optic modulator 20. (Fiber optic modulators such as modulator 20 or compensating coil 19-1 are described in "An All Fiber Optic Device For Dynamic Rotation of the Polarization Plane of a Light Wave", by A. Irace et al., IEEE Journal 0-7803-31-09 dated May 1996, pages 684–686.) Numeral 14B illustrates that optical fiber exiting from fiber optic modulator 20 and passing into a conventional fiber optic splitter 12A from which optical fibers 14C and 14D diverge. Optical fiber 14C terminates in a collimator 13B, from which beam 2E emerges and then passes through sample 22, if it is present in the measurement channel. The beam 2F emerging from the sample 22 enters a collimator 13C, which introduces beam 2F into an optical fiber 14E. Optical fiber 14E can pass directly into a collimator 13E, or can make a number of loops around a torus to form compensating coil 19-1 as shown. In any case, beam 2Z emerges from collimator 13E and passes through analyzer 7. Beam 2J emerges from analyzer 7 and impinges on detector 8.

Optical fiber 14D terminates on collimator 13D, from which beam 2Y emerges and passes through analyzer 7A, and emerges therefrom as beam 2H which impinges on reference channel detector 8A.

FIG. 15 shows an implementation of the polarimeter system shown in FIG. 10B contained in a housing 101 having a recess 102 to allow an ear lobe or fold of skin to be introduced as sample 22 into the measurement path. A sample-receiving space 106 into which the ear lobe or fingertip is inserted is bounded by an extension 103 from recess 102. A moveable section 104 is positioned in recess 102 and can be adjusted in the directions of arrows 105 to determine the width of the sample-receiving space 106. With the ear lobe in space 106, section 104 is adjusted to press the ear lobe between the opposed sides of section 104 and extension 103. This provides a measurement of the width (path length) of the sample through which the measurement beam passes. The width of the sample is used in the determination of glucose concentration from the amount of optical rotation of the measurement beam as it passes through the sample. A variety of linear transducers can be used to provide a measurement of path length. It will be necessary to provide the appropriate drawing and description of the method to be employed in making measurement through the anterior chamber of the eye. Due to individual differences in epidermis thickness and melanin concentration, calibration of the instrument to a specific user may be required. Beam 2E passes through the ear lobe (i.e., sample 22) and emerges therefrom as beam 2F, which is reflected by surface 18A of glass guide 18 to surface 18B and emerges therefrom as beam 2Z.

The structure shown in FIG. 15 could be modified to guide the beam 2F through a portion of the anterior chamber of a human eye which constitutes the sample, and the optical rotation caused by the tissue of the anterior chamber accurately indicates the blood glucose concentration of the patient. In this case an optical method of measuring the path length of the beam across the cornea is used to measure path length.

Figure 16A:
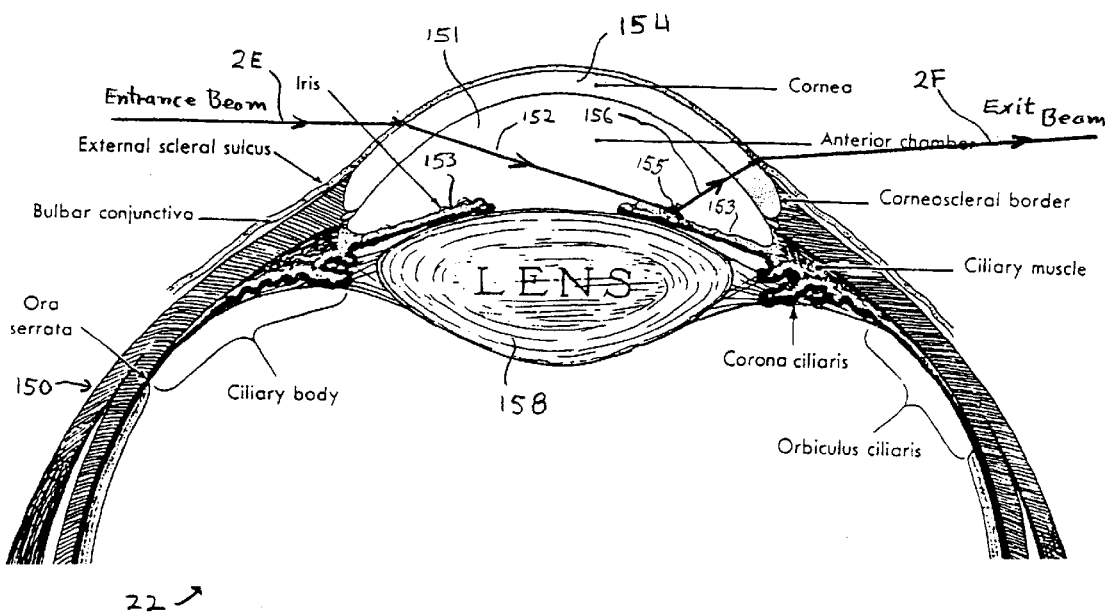
FIGS. 16A–C illustrates the human eye as a sample in any of FIGS. 10A, 10B and 14 for different paths of the entrance beam as it propagates through the acqueous humor.
Figure 16B:
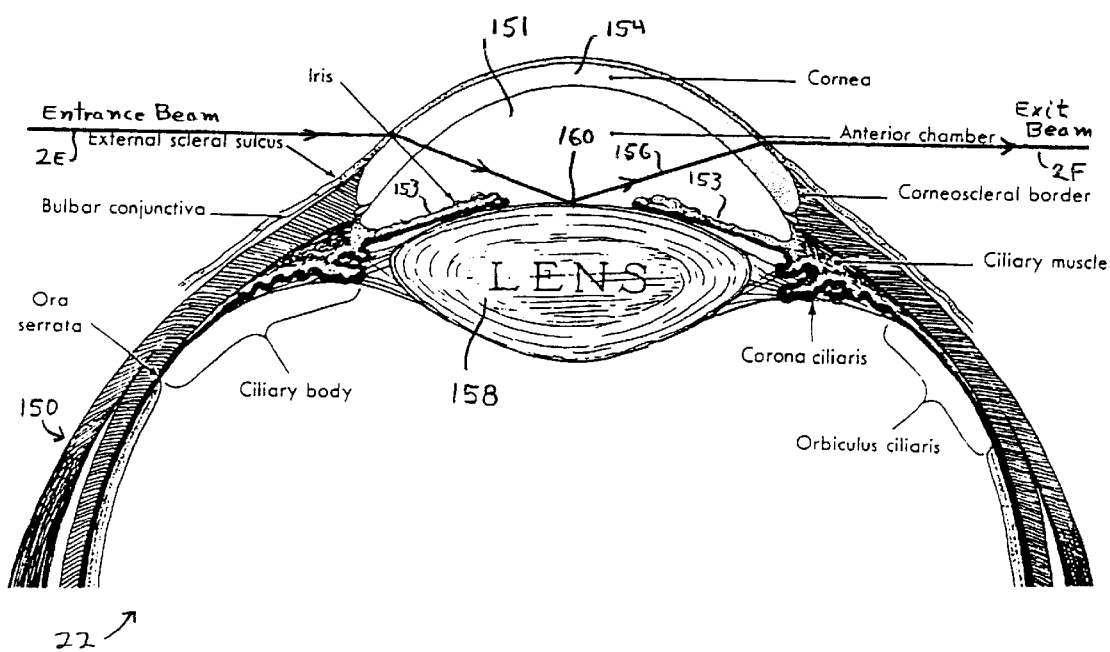
Figure 16C:
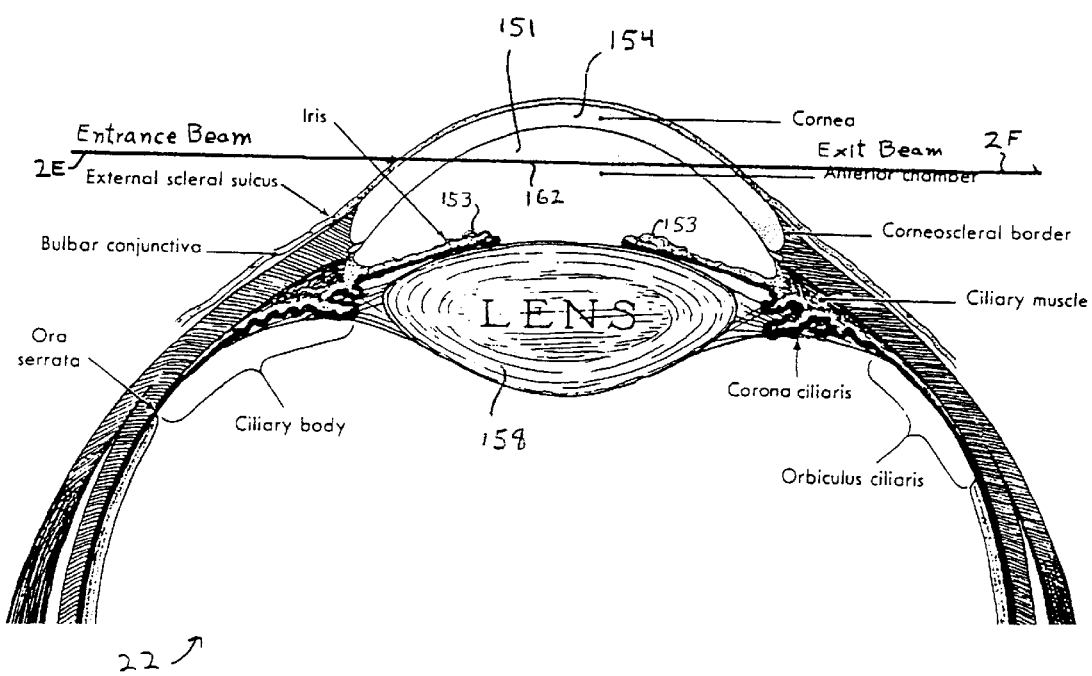

As mentioned above, the sample 22 can be the aqueous humor in the anterior chamber of the human eye, as shown in FIGS. 16A–16C. The entrance beam 2E in FIGS. 16A–C can be the entrance beam 2E shown in any of FIGS. 10A, 10B, or 14, and the exit beam 2F shown in FIGS. 16A–C can be the exit beam 2F shown in any of FIGS. 10A, 10B or 14. The human eye 150 includes an aqueous humor 150, a cornea 154, an iris 153, and a lens 158 (shown in FIGS. 16B and 16C). The entrance beam 2E enters the left side of cornea 154. In FIG. 16A, the entrance beam is refracted to produce beam 152, which propagates to a spot 155 of iris 153. Beam 152 is reflected from spot 155 as reflected beam 156. Reflected beam 156 propagates through aqueous humor 151 to the right side of cornea 154, exits the cornea, and is refracted to produce exit beam 2F.

FIG. 16B shows a different path of the beam transmitted through the aqueous humor 151, wherein entrance beam 2E is refracted as beam 152 which propagates to and is reflected from the lens 158. Beam 152 is reflected as beam 156. Reflected beam 156 propagates through aqueous humor 151 to the right side of cornea 154, exits the cornea, and is refracted as exit beam 2F.

FIG. 16C shows another path of the beam transmitted through aqueous humor 151, wherein the entrance beam 2E enters the cornea 154 and is refracted to produce beam 162. Refracted earn 162 propagates through aqueous humor 151 parallel to iris 153 to the right edge of cornea 154, and is refracted as it leaves cornea 154 to produce exit beam 2F.

While the invention has been described with reference to several particular embodiments thereof, those skilled in the art will be able to make the various modifications to the described embodiments of the invention without departing from the true spirit and scope of the invention. It is intended that all elements or steps which are insubstantially different or perform substantially the same function in substantially the same way to achieve the same result as what is claimed are within the scope of the invention. For example, the technique described above could be used on drawn blood samples, other fluid samples, and tissue.

What is claimed is:

1. A method for polarimetric measurement of optical rotation of light caused by a concentration of a substance contained in a sample, comprising:

(a) providing a laser beam passing through a polarizer and an optical modulator and split into a measurement beam and a reference beam, analyzing the measurement beam and directing it onto a first detector coupled to a first amplifier, and analyzing the reference beam and directing it onto a second detector coupled to a second amplifier;

(b) performing identical filtering at integral multiples of a modulation frequency, and performing multiplication and algebraic summing operations on outputs of the first and second amplifiers to produce a first $\Psi^2/2$ signal and a first $2\beta\Psi$ signal in response to the measurement beam and a second $\Psi^2/2$ signal and a second $2\beta\Psi$ signal in response to the reference beam, $\Psi$ representing a modulation level of light emanating from the optical modulator, and $\beta$ representing optical rotation from extinction of the measurement beam or reference beam;

(c) stabilizing the measurement beam by
  i. comparing the second $\Psi^2/2$ signal to a first reference signal to produce a first error signal,
  ii. comparing the second $2\beta\Psi$ signal to a second reference signal to produce a second error signal,
  iii. multiplying the first error signal by a modulation signal to produce a modulation feedback signal and adding it to the second error signal to produce a combined modulation and zeroing feedback signal, and
  iv. driving the optical modulator in response to the combined modulation and zeroing feedback signal to minimize the first and second error signals; and (d) computing a first value of $\beta$ from the first $\Psi^2/2$ signal and the first $2\beta\Psi$ signal with no sample in a path of the measurement beam and a second value of $\beta$ from the first $\Psi^2/2$ signal and the first $2\beta\Psi$ signal with the sample in the path of the measurement beam, and computing the difference between the first and second values of $\beta$.

2. The method of claim 1 wherein step (a) includes directing the measurement beam to an analyzer by means of a glass guide, and providing a compensation coil around the glass guide, measuring the temperature of the glass guide, and controlling a current in the compensation coil to compensate the temperature coefficient of the Verdet constant of the glass guide.

3. The method of claim 1 wherein each of the first and second $2\beta\Psi$ signals has a value according to the expression $$2\beta\Psi = 1 \cdot Z_1 \cos(\omega t) \cdot 3 \cdot Z_3 \cos(3\omega t) + 5 \cdot Z_5 \cos(5\omega t) - 7 \cdot Z_7 \cos(7\omega t) + \ldots,$$

wherein $\omega t$, $3\omega t$, $5\omega t$ ... represent odd harmonic frequencies, and $Z_1$, $Z_3$, $Z_5$... represent odd harmonic coefficients.

4. The method of claim 3 wherein each of the first and second $\Psi^2/2$ signals has a value according to the expression $$(1/2)\Psi^2 = 1 \cdot Y_2 \cos(2\omega t) - 4 \cdot Y_4 \cos(4\omega t) + 8 \cdot Y_6 \cos(6\omega t) - 16 \cdot Y_8 \cos(8\omega t) + \ldots$$

wherein $2\omega t$, $4\omega t$, $6\omega t$ ... represent even harmonic frequencies, and $Y_2$, $Y_4$, $Y_6$... represent even harmonic coefficients.

5. The method of claim 4 wherein the magnitude of the modulation level of light $\Psi$ corresponds to a modulation angle $\delta$ substantially greater than 45 degrees, and wherein $\Psi \cos(\omega t)$ is the electrical signal applied to the optical modulator to produce the modulation angle $\delta$ of the polarized light.

6. The method of claim 4 wherein the magnitude of the modulation level of light $\Psi$ corresponds to a modulation angle $\delta$ in the range of approximately 30 degrees to 75 degrees, and wherein $\Psi \cos(\omega t)$ is the electrical signal applied to the optical modulator to produce the modulation angle $\delta$ of the polarized light.

7. The method of claim 1 wherein the filtering at integral multiples of the modulation frequency in step (b) is performed by fast Fourier transforms to be used in the multiplication and algebraic summing operations.

8. The method of claim 7 including performing a coherent averaging operation on the fast Fourier transforms to improve the signal-to-noise ratio of the polarimetric measurement.

9. A method for polarimetric measurement of the concentration of a substance contained in a sample, comprising:

(a) providing a laser beam passing through a polarizer and an optical modulator and split into a measurement beam and a reference beam, analyzing the measurement beam, and directing it onto a first detector coupled to a first amplifier, and analyzing the reference beam and directing it onto a second detector coupled to a second amplifier;

(b) performing identical filtering at integral multiples of a modulation frequency, and performing multiplication and algebraic summing operations on outputs of the first and second amplifiers to produce a first $\Psi^2/2$ signal and a first $2\beta\Psi$ signal in response to the measurement beam and a second $\Psi^2/2$ signal and a second $2\beta\Psi$ signal in response to the reference beam, $\beta$ representing a modulation level of light emanating from the optical modulator, and $\Psi$ representing optical rotation from extinction of the measurement beam or reference beam;

(c) stabilizing the measurement beam by
  i. comparing the second $\Psi^2/2$ signal to a first reference signal to produce a first error signal,
  ii. comparing the second $2\beta\Psi$ signal to a second reference signal to produce a second error signal,
  iii. multiplying the first error signal by a modulation signal to produce a modulation feedback signal and adding it to the second error signal to produce a combined modulation and zeroing feedback signal, and
  iv. driving the optical modulator in response to the combined modulation and zeroing feedback signal to minimize the first and second error signals; and (d) computing a first value of $\beta$ from the first $2\beta\Psi$ signal with no sample in a path of the measurement beam and a second value of $\beta$ from the first $2\beta\Psi$ signal with the sample in the path of the measurement beam, and converting the difference between the first and second values of $\beta$ to a value of concentration of the substance in the sample.

10. The method of claim 9 wherein each of the first and second $2\beta\Psi$ signals has a value according to the expression $$2\beta\Psi = 1 \cdot Z_1 \cos(\omega t) - 3 \cdot Z_3 \cos(3\omega t) + 5 \cdot Z_5 \cos(5\omega t) - 7 \cdot Z_7 \cos(7\omega t) + \ldots,$$

wherein $\omega t$, $3\omega t$, $5\omega t$ ... represent odd harmonic frequencies, and $Z_1$, $Z_3$, $Z_5$... represent odd harmonic coefficients.

11. The method of claim 10 wherein the magnitude of the modulation-level of light $\Psi$ corresponds to a modulation angle $\delta$ substantially greater than 45 degrees, and wherein $\Psi \cos(\omega t)$ is the electrical signal applied to the optical modulator to produce the modulation angle $\delta$ of the polarized light.

12. The method of claim 10 wherein the magnitude of the modulation level of light $\Psi$ corresponds to a modulation angle $\delta$ in the range of approximately 30 degrees to 75 degrees, and wherein $\Psi \cos(\omega t)$ is the electrical signal applied to the optical modulator to produce the modulation angle $\delta$ of the polarized light.

13. The method of claim 9 wherein the filtering at integral multiples of the modulation frequency in step (b) is performed by fast Fourier transforms to be used in the multiplication and algebraic summing operations.

14. The method of claim 13 including performing a coherent averaging operation on the fast Fourier transforms to improve the signal-to-noise ratio of the polarimetric measurement.

15. The method of claim 9 wherein step (a) includes directing the measurement beam to an analyzer by means of a first glass guide.

16. The method of claim 15 including providing a compensation coil around the first glass guide, measuring the temperature of the first glass guide, and controlling a current in the compensation coil to compensate for the temperature coefficient of the Verdet constant of the first glass guide.

17. The method of claim 15 including introducing the sample in the path of the measurement beam ahead of the first glass guide.

18. The method of claim 17 wherein the sample is an ear lobe, the method including placing a portion of the first glass guide behind the ear lobe.

19. The method of claim 9 wherein the substance is glucose, and the sample is human tissue.

20. The method of claim 19 wherein step (d) includes using a stored look-up table or an algorithm to convert the difference between the first and second values of $\beta$ to a value of glucose concentration in the sample.

21. The method of claim 9 including converting analog output signals produced by the first amplifier to digital measurement channel signals, and converting analog output signals produced by the second amplifier to digital reference channel signals.

22. The method of claim 21 including performing one of steps (b) and (c) in a digital signal processor operating in response to the digital measurement channel signals and the digital reference channel signals.

23. The method of claim 15 including zeroing a measurement channel including the measurement beam by driving the measurement beam to extinction by means of a compensation coil around the first glass guide with no sample in the measurement channel.

24. A system for polarimetric measurement of the concentration of glucose in a sample, comprising:
  (a) a polarizer;
  (b) an optical modulator;
  (c) a laser producing a laser beam passing through the polarizer and then passing through the optical modulator;
  (d) a beam splitter splitting the beam emanating from the optical modulator into a measurement beam and a reference beam;
  (e) means for analyzing the measurement beam and the reference beam;
  (f) a first detector detecting the analyzed measurement beam, and a second detector detecting the analyzed reference beam;
  (g) a first amplifier amplifying an output of the first detector, and a second amplifier amplifying an output of the second detector;
  (h) means for performing identical filtering at integral multiples of a modulation frequency, and performing multiplication and algebraic summing operations on outputs of the first and second amplifiers to produce a first $\Psi^2/2$ signal and a first $2\beta\Psi$ signal in response to the measurement beam and a second $\Psi^2/2$ signal and a second $2\beta\Psi$ signal in response to the reference beam, $\Psi$ representing a modulation level of light emanating from the optical modulator, and $\beta$ representing optical rotation from extinction of the measurement beam or reference beam;
  (i) means for stabilizing the measurement beam by
    i. comparing the second $\Psi^2/2$ signal to a first reference signal to produce a first error signal,
    ii. comparing the second $2\beta\Psi$ signal to a second reference signal to produce a second error signal,
    iii. multiplying the first error signal by a modulation signal to produce modulation feedback signal and adding it to the second error signal to produce a combined modulation and zeroing feedback signal, and
    iv. driving the optical modulator in response to the combined modulation and zeroing feedback signal to minimize the first and second error signals; and
  (j) means for computing a first value of $\beta$ from the first $2\beta\Psi$ signal with no sample in the path of the measurement beam and a second value of $\beta$ from the first $2\beta\Psi$ signal with the sample in the path of the measurement beam, and converting the difference between the first and second values of $\beta$ to a value of glucose concentration in the sample.

25. A system for polarimetric measurement of the concentration of an optically active substance in a sample, comprising:
  (a) a polarizer;
  (b) an optical modulator;
  (c) a laser producing a laser beam passing through the polarizer and then through the optical modulator;
  (d) a splitter splitting the beam emanating from the optical modulator into a measurement beam and a reference beam;
  (e) a first analyzer in the path of the measurement beam and a second analyzer in the path of the reference beam;
  (f) a first detector detecting the analyzed measurement beam, and a second detector detecting the analyzed reference beam;
  (g) a first amplifier amplifying an output of the first detector, and a second amplifier amplifying an output of the second detector; and
  (h) a digital signal processor adapted to
    i. perform identical filtering at integral multiples of a modulation frequency, and performing multiplication and algebraic summing operations on digital representations of outputs of the first and second amplifiers to produce a first $\Psi^2/2$ signal and a first $2\beta\Psi$ signal in response to the measurement beam and a second $\Psi^2/2$ signal and a second $2\beta\Psi$ signal in response to the reference beam, $\Psi$ representing a modulation level of light emanating from the optical modulator, and $\beta$ representing optical rotation from extinction of the measurement beam or reference beam,
    ii. stabilize the measurement beam by comparing the second $\Psi^2/2$ signal to a first reference signal to produce a first error signal, comparing the second $2\beta\Psi$ signal to a second reference signal to produce a second error signal, multiplying the first error signal by a modulation signal to produce a modulation feedback signal and adding it to the second error signal to produce a combined modulation and zeroing feedback signal, and driving the optical modulator in response to the combined modulation and zeroing feedback signal to minimize the first and second error signals, and
    iii. compute a first value of $\beta$ from the first $2\beta\Psi$ signal with no sample in the path of the measurement beam and a second value of $\beta$ from the first $2\beta\Psi$ signal with the sample in the path of the measurement beam, and converting the difference between the first and second values of $\beta$ to a value of glucose concentration in the sample.

26. The system of claim 25 wherein the substance is glucose, and the sample is human tissue.

27. The system of claim 25 including a first analog-to-digital converter having an input coupled to the output of the first amplifier and an output coupled to a digital input of the digital signal processor, and a second analog-to-digital converter having an input coupled to the output of the second amplifier and an output coupled to the digital input of the digital signal processor.

28. The system of claim 25 including a Faraday glass guide guiding the measurement beam to the first analyzer with a compensation coil around the glass guide, a temperature sensor adapted for measuring the temperature of the glass guide, an analog-to-digital converter coupled between the temperature sensor and the digital signal processor and adapted to convert an output signal produced by the temperature sensor to a digital signal, the digital signal processor compensating the first and second values of $\beta$ for the temperature coefficient of the Verdet constant of the glass guide during computing of the first and second values of $\beta$.

29. The system of claim 28 wherein the system is packaged in a housing including a first section containing a portion of the glass guide, the first section bounding a first side of a recess for receiving an earlobe, finger or the like as the sample, the glass guide guiding the measurement beam through the sample in the recess.

30. The system of claim 29 wherein the housing includes a moveable second section bounding a second side of the recess, to provide a measurement of the width of the sample.

31. The system of claim 30 including a transducer coupled to the moveable second section and adapted to provide a signal representative of the width of the sample to the digital signal processor for use in computing the second value of $\beta$.

* * * * *